(12) United States Patent
Naya et al.

(10) Patent No.: US 7,875,633 B2
(45) Date of Patent: Jan. 25, 2011

(54) PHENYLPYRIDONE DERIVATIVE

(75) Inventors: Akira Naya, Tsukuba (JP); Toshihiro Sakamoto, Moriya (JP); Yuji Haga, Tsukuba (JP); Norikazu Otake, Tsukuba (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 435 days.

(21) Appl. No.: 11/990,889

(22) PCT Filed: Aug. 23, 2006

(86) PCT No.: PCT/JP2006/317024

§ 371 (c)(1), (2), (4) Date: Feb. 22, 2008

(87) PCT Pub. No.: WO2007/024004

PCT Pub. Date: Mar. 1, 2007

(65) Prior Publication Data

US 2009/0137587 A1 May 28, 2009

(30) Foreign Application Priority Data

Aug. 24, 2005 (JP) .............................. 2005-242397

(51) Int. Cl.
| | |
|---|---|
| A61K 31/444 | (2006.01) |
| A61K 31/4439 | (2006.01) |
| A61K 31/5377 | (2006.01) |
| A61K 31/4545 | (2006.01) |
| A61P 9/00 | (2006.01) |
| A61P 25/00 | (2006.01) |
| A61P 3/00 | (2006.01) |
| C07D 213/64 | (2006.01) |
| C07D 401/02 | (2006.01) |
| C07D 413/02 | (2006.01) |
| C07D 401/14 | (2006.01) |

(52) U.S. Cl. ..................... 514/332; 514/235.5; 514/318; 514/333; 514/343; 546/300; 546/261; 546/194; 546/276.4; 546/256; 544/131

(58) Field of Classification Search .............. 514/235.5, 514/318, 333, 332, 343; 546/300, 261, 194, 546/276.4, 256; 544/131
See application file for complete search history.

(56) References Cited

U.S. PATENT DOCUMENTS

| | | | |
|---|---|---|---|
| 7,067,540 B2 * | 6/2006 | Devadas et al. ............. 514/348 |
| 2004/0077628 A1 | 4/2004 | Ishihara et al. | |
| 2005/0049253 A1 | 3/2005 | Tegley | |
| 2005/0209274 A1 | 9/2005 | Lynch et al. | |
| 2006/0106046 A1 | 5/2006 | Moriya et al. | |
| 2006/0287340 A1 | 12/2006 | Moriya et al. | |
| 2007/0208046 A1 | 9/2007 | Otake et al. | |
| 2007/0249659 A1 | 10/2007 | Sakuraba et al. | |
| 2007/0299070 A1 | 12/2007 | Suzuki et al. | |

FOREIGN PATENT DOCUMENTS

| | | |
|---|---|---|
| EP | 1 285 651 A1 | 2/2003 |
| EP | 1 741 703 A1 | 10/2007 |
| EP | 1 876 179 A1 | 1/2008 |
| WO | WO 01/21577 A2 | 3/2001 |
| WO | WO 01/21577 A3 | 3/2001 |
| WO | WO 02/02744 A2 | 1/2002 |
| WO | WO 02/02744 A3 | 1/2002 |
| WO | WO 02/06245 A1 | 1/2002 |
| WO | WO 02/081454 A1 | 10/2002 |
| WO | WO 03/068230 A1 | 8/2003 |
| WO | WO 2005/018557 A2 | 3/2005 |
| WO | WO 2005/018557 A3 | 3/2005 |
| WO | WO 2005/047293 A1 | 5/2005 |

(Continued)

OTHER PUBLICATIONS

Bost. F. et al., "The role of MAPKs in adipocyte differentiation and obesity", Biochimie, vol. 87, pp. 51-56, 2005.

(Continued)

Primary Examiner—Sreeni Padmanabhan
Assistant Examiner—Sahar Javanmard
(74) Attorney, Agent, or Firm—Janet E. Fair; John C. Todaro

(57) ABSTRACT

A compound represented by the formula (I) is contained as an active ingredient:

(I)

wherein $R_1$ and $R_2$ independently represent a hydrogen atom, a lower alkyl group or the like, or $R_1$ together with a nitrogen atom to which L, $Z_2$ and $R_1$ are attached may form an aliphatic nitrogenated heterocyclic group and $R_1$ and $R_2$ together with a nitrogen atom to which they are attached may form an aliphatic nitrogenated heterocyclic group; X represents a methine group or a nitrogen atom; Y represents —$CH_2$—O—, —CH=CH— or the like; $Z_1$ represents a single bond, a $C_{1-4}$ alkylene group or the like; $Z_2$ represents a single bond or a $C_{1-4}$ alkylene group; L represents a methylene group, a $C_{3-8}$ cycloalkylene group or the like; and Ar represents an aromatic carbocyclic group or the like. The compound is useful as a pharmaceutical for a central nerves system disease, a cardiovascular disease or a metabolic disease.

15 Claims, No Drawings

FOREIGN PATENT DOCUMENTS

WO  WO 2006/018117 A1  2/2006
WO  WO 2007/011284 A1  1/2007

OTHER PUBLICATIONS

Browning, A., "Recent developments in the discovery of melanin-concentrating hormone antagonists: novel antiobesity agents", Expert Opinion Tkher. Patents, vol. 14, No. 3, pp. 313-325, 2004.

Carpenter, A. J. et al., "Melanin-concentrating hormone receptor antagonists as potential antiobesity agents", Expert Opin. Ther. Patents, vol. 12, No. 11, pp. 1639-1646, 2002.

Dyke, H. J. et al., "Recent developments in the discovery of MCH-1R antagonists for the treatment of obesity—an update", Expert Opin. Ther. Patents, vol. 15, No. 10, pp. 1303-1313, 2005.

* cited by examiner

PHENYLPYRIDONE DERIVATIVE

CROSS-REFERENCE TO RELATED APPLICATIONS

This application is a U.S. National Phase application under 35 U.S.C. §371 of PCT Application No. PCT/JP2006/317024, filed Aug. 23, 2006, which published as WO 2007/024004 A1 on Jan. 3, 2007, and claims priority under 35 U.S.C. §365(b) from Japanese patent application No. JP2005-242397, filed Aug. 24, 2005.

Technical Field

The present invention relates to a novel phenylpyridone derivative. The compound acts as a melanin concentrating hormone receptor antagonist, and is useful as a preventive, treating or remedial agent for various circular system diseases, nervous system diseases, metabolic diseases, genital diseases, respiratory diseases, digestive diseases, etc.

Background Art

Melanin concentrating hormone (hereafter referred to as "MCH") is a cyclic peptide hormone/neuro-peptide, which was for the first time isolated by Kawauchi, et al., in 1983 from sermon hypophysis. [Nature, Vol. 305, 321 (1983)]. The hormone is known to functionally antagonize for melanin cell stimulating hormone in fishes, to cause concentration of melanin granules in melanophore and participate in body color change [International Review of Cytology, Vol. 126, 1 (1991); Trends in Endocrinology and Metabolism, Vol. 5, 120 (1994)]. Also in mammals, MCH-containing neuron cells are localized in the hypothalamus lateral field and uncertain zone, but their nerve fibers are projecting over a very wide scope in the brain [see The Journal of Comparative Neurology, Vol. 319, 218 (1992)], and MCH is considered to preside over various central functions in living bodies.

Hypothalamus lateral field is known of old as feeding center, and furthermore, recently molecular biological and pharmacological knowledges suggesting participation of MCH in controlling energetic homeostasis are being much accumulated. That is, it has been reported that expression of mRNA, which is an MCH precursor, is accelerated in the brains of ob/ob mice, db/db mice, $A^y$/a mice, Zucker fatty rats which are model animals of hereditary obesity, and in the brains of fasting mice [see Nature, Vol. 380, 243 (1996); Diabetes, Vol. 47, 294 (1998); Biochemical and Biophysical Research Communications, Vol. 268, 88 (2000); Molecular Brain Research, Vol. 92, 43 (2001)].

Acute ventricular administration of MCH to rats was observed to induce accelerated feeding activity [Nature, Vol. 380, 243 (1996)] and chronic administration invites obesity accompanied by polyphagy [see Proceedings of the National Academy of Sciences of the United States of America, Vol. 99, 3240 (2002)]. Moreover, MCH precursor gene-deficient mice show reduced food ingestion or rise in oxygen consumption per body weight compared to wild type mice. Their low body weight due to decrease in body fat was observed [see Nature, Vol. 396, 670 (1998)].

On the contrary, transgenic mice which express excessive MCH precursor develop obesity accompanied by polyphagy and insulin resistance [see The Journal of Clinical Investigation, Vol. 107, 379 (2001)]. Consequently, it is suggested that MCH is an important factor for developing obesity and participates in diseases induced by metabolic disorders or respiratory diseases for which obesity is one risk factor. Besides, MCH is known to participate also in anxiety-causing action, epilepsy, memory, learning, diuretic action, sodium/potassium excretory action, oxytocin secreting action, reproduction and reproductive function [see Peptides, Vol. 17, 171 (1996); Peptides, Vol. 18, 1095 (1997); Peptides, Vol. 15, 757 (1994); Journal of Neuroendocrinology, Vol. 8, 57 (1996); Critical Reviews in Neurobiology, Vol. 8, 221 (1994)].

MCH causes versatile pharmacological actions through MCH receptors which are present mainly in the central nervous system. As receptors of MCH, at least two types of type 1 receptors (MCH-1R or SLC-1) and type 2 receptors (MCH-2R or SLT) are known [see Nature, Vol. 400, 261 (1999); Nature, Vol. 400, 265 (1999); Biochemical and Biophysical Research Communications, Vol. 261, 622 (1999); Nature Cell Biology, Vol. 1, 267 (1999); FEBS Letters, Vol. 457, 522 (1999); Biochemical and Biophysical Research Communications, Vol. 283, 1013 (2001); The Journal of Biological Chemistry, Vol. 276, 20125 (2001); Proceedings of the National Academy of Sciences of the United States of America, Vol. 98, 7564 (2001); Proceedings of the National Academy of Sciences of the United States of America, Vol. 98, 7576 (2001); The Journal of Biological Chemistry, Vol. 276, 34664 (2001); Molecular Pharmacology, Vol. 60, 632 (2001)].

Of those, the pharmacological action observed on rodents is induced mainly via MCH-1R [see Genomics, Vol. 79, 785 (2002)]. Because MCH-1R gene-deficient mice chronically administered with MCH do not develop polyphagy or obesity, it is known that controlling of energy metabolism by MCH is induced via MCH-1R. Furthermore, the deficiency of MCH-1R is known to promote the activity amount of mice [see Proceedings of the National Academy of Sciences of the United States of America, Vol. 99, 3240 (2002)], and its participation in central diseases accompanied by behavioral disorders, for example, attention-deficit hyperactivity disorder, schizophrenia, depression and the like also is strongly suggested [see Molecular Medicine Today, Vol. 6, 43 (2000); Trends in Neuroscience, Vol. 24, 527 (2001)].

It is also reported that an autoantibody to MCH-1R is present in serum of vitiligo vulgaris patients [see The Journal of Clinical Investigation, Vol. 109, 923 (2002)]. Furthermore, expression of MCH-1R in certain species of cancer cells was reported, and in vivo expression sites of MCH and MCH-1R also suggest MCH's participation in cancer, sleep, vigil, drug dependence and digestive disorders [see Biochemical and Biophysical Research Communications, Vol. 289, 44 (2001); Neuroendocrinology, Vol. 61, 348 (1995); Endocrinology, Vol. 137, 561 (1996); The Journal of Comparative Neurology, Vol. 435, 26 (2001)].

Functions of MCH are expressed upon it binding to MCH receptors. Therefore, when its binding to MCH receptor is inhibited, then expression of MCH action can be inhibited. In consequence, substances which are antagonists for binding of MCH with its receptor are useful as preventive, treating or remedial agents for those various diseases in which MCH participates, for example, metabolic disorders such as obesity, diabetes, hormone disorder, hyperlipidemia, gout, fatty liver; cardiovascular disorders such as stenocardia, acute or congestive heart failure, myocardial infarction, coronary atherosclerosis, hypertension, renal diseases, electrolyte abnormality; central and peripheral nervous system disorders such as bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence, alcoholism; reproductive disorders such as infertility, preterm labor and sexual dysfunction; and other digestive disorders, respiratory disorders, cancer or pigmentation et al.

As compounds having an MCH receptor antagonistic effect, for example, various compounds are disclosed in WO01/21577, WO01/82925, WO02/06245, WO02/02744. However, they do not have a pyridone ring.

WO03/68230 (Patent Reference 1) discloses a wide variety of pyridone derivatives having a P38MAP kinase activity. However, in the compound that the present invention discloses, the pyridone ring directly bonds to the benzene ring, the phenyl group adjacent to the pyridone is unsubstituted, and the group with which the pyridone ring may be substituted is a halogen atom alone; but the compounds that satisfy these conditions are not given in the reference, and further, the reference does not describe an MCH receptor antagonistic effect.

Patent Reference 1: WO03/68230

DISCLOSURE OF THE INVENTION

The present inventors have assiduously studied compounds having an MCH receptor antagonistic effect, and as a result, have found that a pyridone derivative, in which a phenyl group directly bonds to the N atom of the pyridone ring and the phenyl group has a specific amino group at the para-position via a linker, has an MCH receptor antagonistic effect and is effective for prevention, treatment or remedy of various MCH receptor-associated diseases, and have completed the present invention.

Specifically, the invention provides:

(1) a phenylpyridone derivative of a formula (I) or a pharmaceutically-acceptable salt thereof:

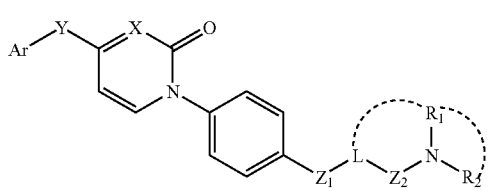

(I)

[wherein:

$R_1$ and $R_2$ are the same or different, each representing a hydrogen atom, or a lower alkyl group optionally having substituent(s), and $R_1$, taken together with L, $Z_2$ and the nitrogen atom adjacent to $R_1$, may form an aliphatic nitrogen-containing hetero ring optionally having substituent(s), and $R_1$ and $R_2$, taken together with the nitrogen atom to which they bond, may form an aliphatic nitrogen-containing hetero ring optionally having substituent(s);

X represents a methine group optionally substituted with a halogen, or a nitrogen atom;

Y represents —$CH_2$—O—, —CH=CH— or —$CH_2$—$CH_2$—;

$Z_1$ represents a single bond, a $C_{1-4}$ alkylene group optionally having substituent(s), a $C_{1-4}$ alkylene-O— optionally having substituent(s), a $C_{1-3}$ alkylene-O—$C_{1-3}$ alkylene group optionally having substituent(s), a $C_{2-4}$ alkenylene group optionally having substituent(s), or —NR—, R represents a hydrogen atom, or a lower alkyl group optionally having substituent(s);

$Z_2$ represents a single bond or a $C_{1-4}$ alkylene group optionally having substituent(s);

L represents a methylene group optionally having substituent(s), or a $C_{3-8}$ cycloalkylene group optionally having substituent(s), or L, taken together with $Z_2$, $R_1$ and the nitrogen atom adjacent to $R_1$, may form an aliphatic nitrogen-containing hetero ring optionally having substituent(s);

provided that, when $Z_1$ and $Z_2$ are single bonds at the same time, then L is not a methylene group;

Ar represents an aromatic carbocyclic group optionally having substituent(s), or an aromatic heterocyclic group optionally having substituent(s)].

The invention further provides:

(2) a melanin concentrating hormone receptor antagonist comprising a compound of (1) or a pharmaceutically-acceptable salt thereof as the active ingredient;

(3) a pharmaceutical composition comprising a pharmaceutically-acceptable additive and a compound of (1) or a pharmaceutically-acceptable salt thereof, (4) a preventive, treating or remedial agent comprising a compound of (1) or a pharmaceutically-acceptable salt thereof as the active ingredient, for metabolic disorders such as obesity, diabetes, hormone disorder, hyperlipidemia, gout, fatty liver, hepatitis, cirrhosis; cardiovascular disorders such as stenocardia, acute or congestive heart failure, myocardial infarction, coronary atherosclerosis, hypertension, renal diseases, electrolyte abnormality; central and peripheral nervous system disorders such as bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence, alcoholism; reproductive disorders such as infertility, preterm labor and sexual dysfunction; digestive disorders; respiratory disorders; cancer or pigmentation.

The invention is described in more detail hereinunder.

In this description, the term "lower" means that the number of the carbon atoms constituting the group or the compound with the term is at most 6, preferably at most 4.

"Lower alkyl group" includes a linear alkyl group having from 1 to 6 carbon atoms or a branched alkyl group having from 3 to 6 carbon atoms, concretely, for example, a methyl group, an ethyl group, an n-propyl group, an isopropyl group, an n-butyl group, an isobutyl group, a sec-butyl group, a tert-butyl group, an n-pentyl group, an isopentyl group, a neopentyl group, a tert-amyl group, a 1-methylbutyl group, a 2-methylbutyl group, a 1,2-dimethylpropyl group, a 1-ethylpropyl group, an n-hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1-ethylbutyl group, a 1,1,2-trimethylpropyl group, a 1,2,2-trimethylpropyl group, a 1-ethyl-2-methylpropyl group, 1-ethyl-1-methylpropyl group et al.

"Lower cycloalkyl group" includes a cycloalkyl group having from 3 to 6 carbon atoms, concretely, for example, a cyclopropyl group, a cyclobutyl group, a cyclopentyl group, a cyclohexyl group.

"Lower alkylene group" includes a linear alkylene group having from 1 to 6 carbon atoms or a branched alkylene group having from 3 to 6 carbon atoms, concretely, for example, a methylene group, an ethylene group, a propylene group, a butylene group, a pentylene group, a hexylene group et al.

"Lower alkenylene group" includes a linear alkenylene group having from 2 to 6 carbon atoms or a branched alkenylene group having from 3 to 6 carbon atoms, having one carbon-carbon double bond in the chain, concretely, for example, a vinylene group, a 1-propenylene group, a 2-propenylene group, a 1-butenylene group, a 2-butenylene group, a 3-butenylene group, a 2-pentenylene group, a 3-pentenylene group, a 4-pentenylene group, a 1-hexenylene group, a 2-hexenylene group, a 3-hexenylene group, a 4-hexenylene group, a 5-hexenylene group et al.

"Lower cycloalkylene group" includes a cycloalkylene group having from 3 to 6 carbon atoms, concretely, for example, a 1,1-cyclopropylene group, a 1,2-cyclopropylene group, a 1,1-cyclobutanylene group, a 1,2-cyclobutanylene group, a 1,3-cyclobutanylene group, a 1,1-cyclopentenylene group, a 1,2-cyclohexenylene group, a 1,3-cyclohexenylene group, a 1,4-cyclohexenylene group et al.

Examples of the substituent in "lower alkyl group optionally having substituent(s)", "$C_{1-4}$ alkylene group optionally having substituent(s)", "$C_{1-4}$ alkylene-O— optionally having substituent(s)", "$C_{1-3}$ alkylene-O—$C_{1-3}$ alkylene optionally having substituent(s)", "$C_{2-4}$ alkenylene group optionally having substituent(s)" and "$C_{3-8}$ cycloalkylene group optionally having substituent(s)" may be those selected from a group α; and the above-mentioned lower alkyl group and others may be substituted with one or more such substituents. Substituent selected from group α:

A halogen atom, a cyano group, a hydroxyl group, an amino group, a lower alkyl group optionally substituted with a fluorine atom or a hydroxyl group, a mono-lower alkylamino group, a di-lower alkylamino group, a lower alkyloxy group optionally substituted with a fluorine atom, a lower alkyloxy-lower alkyl group, a lower alkyloxycarbonyl group, a lower alkyloxycarbonylamino group, a lower alkyloxycarbonyl(lower alkyl)amino group, a lower alkylcarbonyl group, a lower alkylcarbonyloxy group, a lower alkylcarbonylamino group, a lower alkylcarbonyl(lower alkyl)amino group, a carbamoyl group, a mono-lower alkylcarbamoyl group, a di-lower alkylcarbamoyl group, a carbamoylamino group, a mono-lower alkylcarbamoylamino group, a di-lower alkylcarbamoyl amino group, a mono-lower alkylcarbamoyl (lower alkyl)amino group, a di-lower alkylcarbamoyl(lower alkyl)amino group, a carbamoyloxy group, a mono-lower alkylcarbamoyloxy group, a di-lower alkylcarbamoyloxy group, a lower alkylsulfonyl group, a lower alkylsulfonylamino group, a lower alkylsulfonyl(lower alkyl)amino group, a sulfamoyl group, a mono-lower alkylsulfamoyl group, a di-lower alkylsulfamoyl group, a sulfamoylamino group, a mono-lower alkylsulfamoylamino group, a di-lower alkylsulfamoylamino group, a mono-lower alkylsulfamoyl (lower alkyl)amino group, and a di-lower alkylsulfamoyl (lower alkyl)amino group.

"Aliphatic nitrogen-containing heterocyclic group" includes a 3- to 7-membered monocyclic, or 5 to 12-membered polycyclic, saturated or partially-unsaturated heterocyclic group, containing at least one, preferably from 1 to 3 nitrogen atoms as a part of the ring-constitutive members, and optionally containing from 0 to 2 oxygen atoms or from 0 to 2 sulfur atoms; and concretely, for example, it includes an aziridinyl group, an azetidinyl group, a pyrrolidinyl group, a piperidinyl group, a homopiperazinyl group, a homopiperidinyl group, a morpholinyl group, a thiomorpholinyl group, an octahydrocyclopenta[b]pyrrolyl group, a hexahydropyrrolidinyl group, an octahydroindolidinyl group, an octahydroquinolidinyl group, an octahydropyrido[2.1-c]oxazinyl group, a 2,5,6,7-tetrahydro-5H-pyrrolo[1.2-a]imidazolyl group et al.

"Aromatic carbocyclic group" includes a monocyclic or polycyclic aromatic carbocyclic group having from 6 to 14 carbon atoms, preferably from 6 to 10 carbon atoms, concretely, for example, a phenyl group, a naphthyl group, a phenanthryl group et al.

"Aromatic heterocyclic group" includes a 5- or 6-membered monocyclic or 8- to 14-membered polycyclic heteroaromatic cyclic group containing at least one, preferably from 1 to 5 hetero atoms selected from a nitrogen atom, an oxygen atom and a sulfur atom as a part of the ring-constitutive members; and concretely, for example, it includes a pyridinyl group, a pyrimidinyl group, a pyridazinyl group, a pyrazyl group, a pyrazolyl group, a pyrrolyl group, an imidazolyl group, a triazolyl group, an oxazolyl group, an isoxazolyl group, an oxadiazolyl group, a thiazolyl group, an isothiazolyl group, a thiadiazolyl group, a tetrazolyl group, a pyridazinyl group, a pyrazinyl group, a furyl group, a thienyl group, an indolyl group, a benzofuranyl group, a benzothienyl group, a benzimidazolyl group, a benzoxazolyl group, a benzisoxazolyl group, a benzothiazolyl group, a benzisothiazolyl group, an indazolyl group, a purinyl group, a quinolyl group, an isoquinolyl group, a phthalazinyl group, a naphthyridinyl group, a quinoxalinyl group, a quinazolinyl group, a cinnolinyl group, a pteridinyl group, a pyrido[3,2-b]pyridyl group et al.

"Aliphatic carbocyclic group" includes a monocyclic or polycyclic, saturated or partially-unsaturated carbocyclic group having from 3 to 10, preferably from 3 to 8 carbon atoms, concretely, for example, a cyclopropyl group, a cyclobutenyl group, a cyclopentyl group, a cyclohexyl group, a cycloheptyl group, a cyclooctyl group, a cyclononyl group, a cyclodecyl group, a bicyclohexyl group, an adamantyl group et al.

Examples of the substituent in "aromatic heterocyclic group optionally having substituent(s)" or "aromatic carbocyclic group optionally having substituent(s)" may be those selected from the group α.

The substituent in "aliphatic nitrogen-containing heterocyclic group optionally having substituent(s)" or "aliphatic carbocyclic group optionally having substituent(s)" includes, in addition to the substituents selected from the group α, an oxo group; and the above-mentioned cyclic groups may be substituted with one or more such substituents.

The substituent in "lower alkyl group optionally having substituent(s)" defined for R is, for example, preferably a halogen atom, a lower alkoxy group, a lower haloalkoxy group.

In the definition of the above-mentioned substituents, "halogen atom" includes a fluorine atom, a chlorine atom, a bromine atom and an iodine atom.

"Oxo group" means a group (=O) that forms a carbonyl group (C=O) along with the carbon atom in an organic compound.

"Lower alkyl group optionally substituted with fluorine atom(s) or hydroxyl group" includes a lower alkyl group, or a lower alkyl group in which a part or all of the hydrogen atoms are substituted with fluorine atom(s) or hydroxyl group; The latter lower alkyl group substituted with fluorine atom(s) or hydroxyl group(s) includes, for example, a fluoromethyl group, a difluoromethyl group, a trifluoromethyl group, a 2-fluoroethyl group, a 1,2-difluoroethyl group, a 2-hydroxyethyl group, a 1,2-dihydroxyethyl group et al.

"Lower alkyloxy group optionally substituted with a fluorine atom" includes a group composed of a lower alkyl group or a lower alkyl group substituted with fluorine atom(s), bonding to an oxygen atom. Concretely, the lower alkyloxy group includes a methoxy group, an ethoxy group, an n-propyloxy group, an isopropyloxy group, a n-butoxy group, an isobutoxy group, a tert-butoxy group, a n-pentyloxy group et al; and the lower alkyloxy group substituted with fluorine atom(s) includes, for example, a fluoromethoxy group, a difluoromethoxy group, a trifluoromethoxy group, a 1,2-difluoroethoxy group et al.

"Mono-lower alkylamino group" is an amino group (—$NH_2$) in which one hydrogen atom is substituted with a lower alkyl group, concretely, for example, including a methylamino group, an ethylamino group, a n-propylamino group, an isopropylamino group, a n-butylamino group, a sec-butylamino group, a tert-butylamino group et al.

"Di-lower alkylamino group" is an amino group (—NH$_2$) in which two hydrogen atoms are substituted with lower alkyl groups, concretely, for example, including a dimethylamino group, a diethylamino group, an ethylmethylamino group, a di(n-propyl)amino group, a methyl(n-propyl)amino group, a diisopropylamino group et al.

"Lower alkyloxy-lower alkyl group" is a lower alkyl group substituted with a lower alkyloxy group, and concretely includes, for example, a methoxymethyl group, an ethoxymethyl group, a n-propyloxymethyl group, an isopropyloxymethyl group, a 1-methoxyethyl group, a 2-methoxyethyl group et al.

"Lower alkyloxycarbonyl group" is a lower alkyloxy group bonding to a carbonyl group (—CO—) and includes an alkyloxycarbonyl group having from 1 to 6 carbon atoms, concretely, for example, a methoxycarbonyl group, an ethoxycarbonyl group, a n-propyloxycarbonyl group, an isopropyloxycarbonyl group, a n-butoxycarbonyl group, an isobutoxycarbonyl group, a tert-butoxycarbonyl group, a n-pentyloxycarbonyl group et al.

"Lower alkyloxycarbonylamino group" is a group of an amino group (—NH$_2$) to which a lower alkyloxycarbonyl group bonds, and includes an alkyloxycarbonylamino group having from 1 to 6 carbon atoms, concretely, for example, a methoxycarbonylamino group, an ethoxycarbonylamino group, a n-propyloxycarbonylamino group, an isopropyloxycarbonylamino group, a n-butoxycarbonylamino group, an isobutoxycarbonylamino group, a tert-butoxycarbonylamino group, a n-pentyloxycarbonylamino group et al.

"Lower alkyloxycarbonyl(lower alkyl)amino group" is a group of a mono-lower alkylamino group in which the hydrogen atom on the nitrogen atom is substituted with a lower alkyloxycarbonyl group and concretely includes, for example, a methoxycarbonyl(methyl)amino group, an ethoxycarbonyl(methyl)amino group, a n-propyloxycarbonyl(methyl)amino group et al.

"Lower alkylcarbonyl group" is a group in which a lower alkyl group is bonded to a carbonyl group (—CO—), and includes an alkylcarbonyl group having from 1 to 6 carbon atoms, concretely, for example, an acetyl group, a propionyl group, a butyryl group, an isobutyryl group, a valeryl group, an isovaleryl group, a pivaloyl group et al.

"Lower alkylcarbonyloxy group" is a lower alkylcarbonyl group bonding to an oxygen atom, and concretely includes, for example, an acetoxy group, a propionyloxy group, a valeryloxy group, an isovaleryloxy group, a pivaloyloxy group et al.

"Lower alkylcarbonylamino group" is a group of an amino group (—NH$_2$) in which one hydrogen atom is substituted with a lower alkylcarbonyl group, and concretely includes, for example, an acetamido group, a propionylamino group, an isobutyrylamino group, a valerylamino group, an isovalerylamino group, a pivaloylamino group et al.

"Lower alkylcarbonyl(lower alkyl)amino group" is a mono-lower alkylamino group in which the hydrogen atom on the nitrogen atom is substituted with a lower alkylcarbonyl, and includes, for example, a methylcarbonyl(methyl)amino group, an ethylcarbonyl(methyl)amino group, a n-propylcarbonyl(methyl)amino group et al.

"Mono-lower alkylcarbamoyl group" is a carbamoyl group (—CONH$_2$) in which one hydrogen atom is substituted with a lower alkyl group, and concretely includes, for example, a methylcarbamoyl group, an ethylcarbamoyl group, a n-propylcarbamoyl group, an isopropylcarbamoyl group, a n-butylcarbamoyl group, a sec-butylcarbamoyl group, a tert-butylcarbamoyl group et al.

"Di-lower alkylcarbamoyl group" is a carbamoyl group (—CONH$_2$) in which two hydrogen atoms are substituted with lower alkyl groups, and concretely includes, for example, a dimethylcarbamoyl group, a diethylcarbamoyl group, an ethylmethylcarbamoyl group, a di(n-propyl)carbamoyl group, a methyl(n-propyl)carbamoyl group, a diisopropylcarbamoyl group et al.

"Mono-lower alkylcarbamoylamino group" is an amino group (—NH$_2$) in which one hydrogen atom is substituted with a mono-lower alkylcarbamoyl group, and concretely includes, for example, a methylcarbamoylamino group, an ethylcarbamoylamino group, a n-propylcarbamoylamino group, an isopropylcarbamoylamino group, a n-butylcarbamoylamino group, a sec-butylcarbamoylamino group, a tert-butylcarbamoylamino group et al.

"Di-lower alkylcarbamoylamino group" is an amino group (—NH$_2$) in which one hydrogen atom is substituted with a di-lower alkylcarbamoyl group, and concretely includes, for example, a dimethylcarbamoylamino group, a diethylcarbamoylamino group, a di(n-propyl)carbamoylamino group, a diisopropylcarbamoylamino group, a di(n-butyl)carbamoylamino group, a di(sec-butyl)carbamoylamino group, a di(tert-butyl)carbamoylamino group et al.

"Mono-lower alkylcarbamoyl(lower alkyl)amino group" is a mono-lower alkylamino group in which the hydrogen atom on the nitrogen atom is substituted with a mono-lower alkylcarbamoyl group, and concretely includes, for example, a monomethylcarbamoyl(methyl)amino group, a monoethylcarbamoyl(methyl)amino group, a [mono(n-propyl)carbamoyl](methyl)amino group et al.

"Di-lower alkylcarbamoyl(lower alkyl)amino group" is a mono-lower alkylamino group in which the hydrogen atom on the nitrogen atom is substituted with a di-lower alkylcarbamoyl group, and concretely includes, for example, a dimethylcarbamoyl(methyl)amino group, a diethylcarbamoyl(methyl)amino group, a [di(n-propyl)carbamoyl](methyl)amino group et al.

"Mono-lower alkylcarbamoyloxy group" is a mono-lower alkylcarbamoyl group bonding to an oxygen atom, and concretely includes, for example, a methylcarbamoyloxy group, an ethylcarbamoyloxy group, a n-propylcarbamoyloxy group, an isopropylcarbamoyloxy group, an n-butylcarbamoyloxy group, a sec-butylcarbamoyloxy group, a tert-butylcarbamoyloxy group et al.

"Di-lower alkylcarbamoyloxy group" is a di-lower alkylcarbamoyl group bonding to an oxygen atom, and concretely includes, for example, a dimethylcarbamoyloxy group, a diethylcarbamoyloxy group, an ethylmethylcarbamoyloxy group, a di(n-propyl)carbamoyloxy group, a methyl(n-propyl)carbamoyloxy group, a diisopropylcarbamoyloxy group et al.

"Lower alkylsulfonyl group" is a lower alkyl group bonding to a sulfonyl group (—SO$_2$), and concretely includes, for example, a methylsulfonyl group, an ethylsulfonyl group, a n-propylsulfonyl group, an isopropylsulfonyl group, a n-butylsulfonyl group, a sec-butylsulfonyl group, a tert-butylsulfonyl group et al.

"Lower alkylsulfonylamino group" is an amino group (—NH$_2$) in which one hydrogen atom is substituted with a lower alkylsulfonyl group, and concretely includes, for example, a methylsulfonylamino group, an ethylsulfonylamino group, a n-propylsulfonylamino group, an isopropylsulfonylamino group, a n-butylsulfonylamino group, a sec-butylsulfonylamino group, a tert-butylsulfonylamino group et al.

"Lower alkylsulfonyl(lower alkyl)amino group" is a group of a mono-lower alkylamino group in which the hydrogen atom on the nitrogen atom is substituted with a lower alkylsulfonyl group, and concretely includes, for example, a methanesulfonyl group, an ethanesulfonyl group, a n-propanesulfonyl group, an isopropanesulfonyl group et al.

"Mono-lower alkylsulfamoyl group" is a group of a sulfamoyl group ($-SO_2NH_2$) in which one hydrogen atom is substituted with a lower alkyl group, and concretely includes, for example, a monomethylsulfamoyl group, a monoethylsulfamoyl group, a mono(n-propyl)sulfamoyl group, a monoisopropylsulfamoyl group, a mono(n-butyl)sulfamoyl group, a mono(sec-butyl)sulfamoyl group, a mono(tert-butyl)sulfamoyl group et al.

"Di-lower alkylsulfamoyl group" is a group of a sulfamoyl group ($-SO_2NH_2$) in which two hydrogen atoms are substituted with lower alkyl groups, and concretely includes, for example, a dimethylsulfamoyl group, a diethylsulfamoyl group, a di(n-propyl)sulfamoyl group, a diisopropylsulfamoyl group, a di(n-butyl)sulfamoyl group, a di(sec-butyl)sulfamoyl group, a di(tert-butyl)sulfamoyl group et al.

"Mono-lower alkylsulfamoylamino group" is a group of an amino group ($-NH_2$) in which one hydrogen atom is substituted with a mono-lower alkylsulfamoyl group, and concretely includes, for example, a (monomethylsulfamoyl)amino group, a (monoethylsulfamoyl)amino group, a [mono(n-propyl)sulfamoyl]amino group, a (monoisopropylsulfamoyl)amino group, a [mono(n-butyl)sulfamoyl]amino group, a [(mono-sec-butyl)sulfamoyl]amino group, a [mono-(tert-butyl)sulfamoyl]amino group et al.

"(Di-lower alkylsulfamoyl)amino group" is a group of an amino group ($-NH_2$) in which one hydrogen atom is substituted with a di-lower alkylsulfamoyl group, and concretely includes, for example, a (dimethylsulfamoyl)amino group, a (diethylsulfamoyl)amino group, an (ethylmethylsulfamoyl)amino group, a [di(n-propyl)sulfamoyl]amino group, a [methyl(n-propyl)sulfamoyl]amino group, a (diisopropylsulfamoyl)amino group et al.

"Mono-lower alkylsulfamoyl(lower alkyl)amino group" is a group of a mono-lower alkylamino group in which the hydrogen atom on the nitrogen atom is substituted with a mono-lower alkylsulfamoyl group, and concretely includes, for example, a monomethylsulfamoyl(methyl)amino group, a monoethylsulfamoyl(methyl)amino group, a [mono(n-propyl)sulfamoyl](methyl)amino group et al.

"Di-lower alkylsulfamoyl(lower alkyl)amino group" is a group of a mono-lower alkylamino group in which the hydrogen atom on the nitrogen atom is substituted with a di-lower alkylsulfamoyl group, and concretely includes, for example, a dimethylsulfamoyl(methyl)amino group, a diethylsulfamoyl(methyl)amino group, a [di(n-propyl)sulfamoyl](methyl)amino group et al.

"Pharmaceutically-acceptable salts" of a phenylpyridone derivative of formula [I] mean ordinary salts that are acceptable as medicines. Their examples are acid-addition salts to the amine moiety of the compound of formula (I) or acid-addition salts to the nitrogen-containing hetero ring thereof, or base-addition salts to the carboxyl group, if any, of the compound of formula (I).

The acid-addition salts include inorganic acid salts such as hydrochlorides, sulfates, nitrates, phosphates, perchlorates et al; organic acid salts such as maleates, fumarates, tartrates, citrates, ascorbates, trifluoroacetates et al; and sulfonates such as methanesulfonates, isethionates, benzenesulfonates, p-toluenesulfonates et al.

The base-addition salts include alkali metal salts such as sodium salts, potassium salts et al; alkaline earth metal salts such as calcium salts, magnesium salts et al; ammonium salts; and organic amine salts such as trimethylamine salts, triethylamine salts, dicyclohexylamine salts, ethanolamine salts, diethanolamine salts, triethanolamine salts, procaine salts, N,N'-dibenzylethylenediamine salts et al.

BEST MODE FOR CARRYING OUT THE INVENTION

For the purpose of more concretely disclosing the phenylpyridone derivatives of the invention hereinunder, various symbols used in formula [I] are described in detail with reference to their examples.

In formula (I), X represents a methine group optionally substituted with a halogen, or a nitrogen atom, preferably a methine group optionally substituted with a halogen, more preferably an unsubstituted methine group.

Y represents $-CH_2-O-$, $-CH=CH-$ or $-CH_2-CH_2-$, preferably $-CH_2-O-$ or $-CH=CH-$.

$Z_1$ represents a single bond, a $C_{1-4}$ alkylene group optionally having substituent(s), a $C_{1-4}$ alkylene-O— optionally having substituent(s), a $C_{1-3}$ alkylene-O—$C_{1-3}$ alkylene group optionally having substituent(s), a $C_{2-4}$ alkenylene group optionally having substituent(s), or $-NR-$, R represents a hydrogen atom, or a lower alkyl group optionally having substituent(s).

The bonding mode of $C_{1-4}$ alkylene-O— is $-C_{1-4}$ alkylene-O-L-$Z_2$-.

$Z_1$ is preferably a single bond, a methylene group optionally having substituent(s), an ethylene group optionally having substituent(s), a methylene-O— optionally having substituent(s), a methylene-O-methylene group optionally having substituent(s), an ethylene-O-optionally having substituent(s), a vinylene optionally having substituent(s); more preferably a single bond, or a methylene group optionally substituted with a lower alkyloxy group, a methylene-O—, a methylene-O-methylene group or a vinylene group; even more preferably a single bond, a methylene group optionally substituted with a methoxy group, a methylene-O—, a methylene-O-methylene group or a vinylene group.

$Z_2$ represents a single bond or a $C_{1-4}$ alkylene group optionally having substituent(s).

$Z_2$ is preferably a single bond, or a methylene group optionally having substituent(s), more preferably a single bond or a methylene group.

L represents:

(a1) a methylene group optionally having substituent(s), or a $C_{3-8}$ cycloalkylene group optionally having substituent(s), or (a2) taken together with $Z_2$, $R_1$ and the nitrogen atom adjacent to $R_1$, L forms an aliphatic nitrogen-containing hetero ring optionally having substituent(s).

However, when $Z_1$ and $Z_2$ are single bonds at the same time, then L is not a methylene group;

(a1) L is preferably a methylene group optionally having substituent(s), or a $C_{4-6}$ cycloalkylene group optionally having substituent(s), more preferably a methylene group optionally having substituent(s), or a cyclobutylene group optionally having substituent(s), even more preferably a methylene group optionally substituted with a methyl group or a cyclobutylene group.

Preferred combinations of -Z$_1$-L-Z$_2$- are:
—CH=CH—CH$_2$—
—CH$_2$—CH$_2$—CH$_2$—
—CH$_2$—CH$_2$—
—CH$_2$—CH(CH$_3$)—
—CH(OCH$_3$)—CH$_2$—
—CH$_2$—O—CH$_2$—CH$_2$—
—NH—CH$_2$—CH$_2$—
—N(CH$_3$)—CH$_2$—CH$_2$—, and

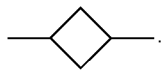

(a2) Preferred examples of the case where L, taken together with Z$_2$ and R$_1$ and with the nitrogen atom adjacent to R$_1$, forms an aliphatic nitrogen-containing hetero ring optionally having substituent(s) are an azetidinyl optionally having substituent(s), a pyrrolidinyl optionally having substituent(s), and a piperidinyl optionally having substituent(s); more preferably a pyrrolidinyl and a piperidinyl substituted with a lower alkyl group; even more preferably a pyrrolidinyl substituted with an isopropyl group and an unsubstituted piperidinyl.

When L-Z$_2$-N—R$_1$, forms a ring, preferred examples of Z$_1$ are a single bond, —CH$_2$—O—, —CH$_2$—O—CH$_2$— et al.

R$_1$ and R$_2$ are the same or different, each representing:

(b1) a hydrogen atom, or a lower alkyl group optionally having substituent(s), (b2) R$_1$, taken together with L, Z$_2$ and the nitrogen atom adjacent to R$_1$, may form an aliphatic nitrogen-containing hetero ring optionally having substituent(s), and (b3) R$_1$ and R$_2$, taken together with the nitrogen atom to which they bond, may form an aliphatic nitrogen-containing hetero ring optionally having substituent(s).

Examples of the substituent with which the "lower alkyl group optionally having substituent(s)" for R$_1$ and R$_2$ may be substituted are selected from those of the group α and a pyridyl group; preferably a halogen such as a fluorine atom, a chlorine atom; a lower alkyloxy group such as a methoxy group, an ethoxy group et al; a lower alkyloxy-lower alkyl group such as a methoxymethyl group, a methoxyethyl group; a pyridyl group et al.

Examples of the substituent with which the aliphatic nitrogen-containing hetero ring may be substituted include those selected from the group α and an oxo group; preferably a lower alkyloxy group, a lower alkyloxyalkyl group, a lower alkyl group, a halogen atom; more preferably a methoxy group, a fluorine atom, a methoxymethyl group et al.

(b1) Preferred examples of R$_1$ and R$_2$ are the same or different, representing a hydrogen, a methyl group, an ethyl group, an isopropyl group, an n-propyl group, an n-butyl group, a 2-pyridylmethyl group et al.

(b2) Preferred examples of the aliphatic nitrogen-containing hetero ring optionally having substituent(s), which is formed by R$_1$, L, Z$_2$ and the nitrogen atom adjacent to R$_1$ are those described in (a2).

(b3) Preferred examples of the aliphatic nitrogen-containing hetero cyclic group optionally having substituent(s), which is formed by R$_1$ and R$_2$ together with the nitrogen atom to which they bond, are an azetidinyl optionally having substituent(s), a pyrrolidinyl optionally having substituent(s), a piperidinyl optionally having substituent(s); more preferably a pyrrolidinyl substituted with a lower alkyloxy group, a lower alkyloxy-lower alkyl group, a lower alkyl group or a halogen atom, or an unsubstituted pyrrolidinyl; even more preferably a pyrrolidinyl substituted with a methoxy group, a fluorine atom, a methoxymethyl group or an isopropyl group, or an unsubstituted pyrrolidinyl.

Ar represents an aromatic carbocyclic group optionally having substituent(s), or an aromatic heterocyclic group optionally having substituent(s).

Examples of the substituent of Ar are selected from those of the group α, preferably a fluorine atom, a chlorine atom, a methyl group, an ethyl group, a trifluoromethyl group, a difluoromethoxy group, a trifluoromethoxy group et al.

Ar includes phenyl, naphthyl, pyridinyl, pyrimidinyl, pyridazinyl, pyrazyl, pyrazole, pyrrolyl, imidazolyl, triazolyl, oxazolyl, isoxazolyl, oxadiazolyl, thiazolyl, isothiazolyl, thiadiazolyl, tetrazolyl, cyclopentyl, cyclohexyl, cycloheptyl, cyclooctyl et al.

In particular, especially preferred are a phenyl group optionally having substituent(s), and a pyridinyl group optionally having substituent(s); more preferred are phenyl, 4-chlorophenyl, 4-fluorophenyl, 4-trifluoromethoxyphenyl, 2-pyridinyl, 5-fluoro-2-pyridinyl, 5-chloro-2-pyridinyl et al.

Preferred examples of the compounds of the invention are:
4-[(4-chlorobenzyl)oxy]-1-(4-{(1E)-3-[ethyl(methyl)amino]-1-propen-1-yl}phenyl)pyridin-2(1H)-one,
4-[(4-chlorobenzyl)oxy]-1-(4-{(1E)-3-[propyl(methyl)amino]-1-propen-1-yl}phenyl)pyridin-2(1H)-one,
4-[(4-chlorobenzyl)oxy]-1-(4-{(1E)-3-[isopropyl(methyl)amino]-1-propen-1-yl}phenyl)pyridin-2(1H)-one,
4-[(4-chlorobenzyl)oxy]-1-(4-{(1E)-3-[butyl(methyl)amino]-1-propen-1-yl}phenyl)pyridin-2(1H)-one,
4-[(4-chlorobenzyl)oxy]-1-(4-[(1E)-3-(dimethylamino)-1-propen-1-yl]phenyl)pyridin-2(1H)-one,
4-[(4-fluorobenzyl)oxy]-1-{4-[(2-pyrrolidin-1-ylethyl)amino]phenyl}pyridin-2(1H)-one,
4-[(4-fluorobenzyl)oxy]-1-(4-{2-[(3S)-3-methoxypyrrolidin-1-yl]ethyl}phenyl)pyridin-2(1H)-one,
4-[(5-chloropyridin-2-yl)methoxy]-1-{4-[2-(diethylamino)ethyl]phenyl}pyridin-2(1H)-one,
4-[(5-chloropyridin-2-yl)methoxy]-1-{4-[(2-cyclopentylamino)ethyl]phenyl}pyridin-2(1H)-one, and
4-[(4-fluorobenzyl)oxy]-1-[4-(trans-3-pyrrolidin-1-ylcyclobutyl)phenyl]pyridin-2(1H)-one, et al.

More preferred are:
4-[(4-chlorobenzyl)oxy]-1-(4-{(1E)-3-[propyl(methyl)amino]-1-propen-1-yl}phenyl)pyridin-2(1H)-one,
4-[(4-chlorobenzyl)oxy]-1-(4-{(1E)-3-[butyl(methyl)amino]-1-propen-1-yl}phenyl)pyridin-2(1H)-one,
4-[(4-fluorobenzyl)oxy]-1-{4-[(2-pyrrolidin-1-ylethyl)amino]phenyl}pyridin-2(1H)-one,
4-[(5-chloropyridin-2-yl)methoxy]-1-{4-[(2-cyclopentylamino)ethyl]phenyl}pyridin-2(1H)-one, and
4-[(4-fluorobenzyl)oxy]-1-[4-(trans-3-pyrrolidin-1-ylcyclobutyl)phenyl]pyridin-2(1H)-one, et al.

Production Methods for Compounds of Formula (I)

The compounds of formula (I) can be produced, for example, according to the following production methods. However, the production methods for the compounds of the invention are not limited to these reaction examples.

Production Method 1:

Production method 1 is for producing a compound of a formula (IV), in which when A in formula (IV) is Arp-Y— and E is (a), the method is for producing a compound of formula (Ip) or formula (I).

Reaction Formula 1

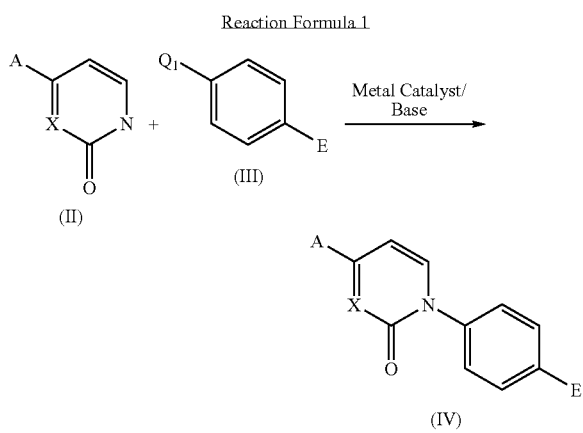

[In the formula, A represents Arp-Y—, $P_2$—O— or a methyl group;

E represents the following formula:

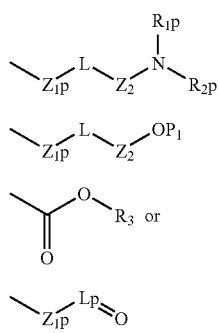

(wherein $Z_1p$ represents $Z_1$ optionally having a protective group; $P_1$ represents a hydrogen atom or a hydroxyl-protective group; $R_1p$ represents $R_1$ optionally having a protective group; $R_2p$ represents $R_2$ optionally having a protective group; $R_3$ represents a hydrogen atom, or a lower alkyl group having from 1 to 6 carbon atoms; Lp represents a group derived from L by removing one hydrogen atom; $Z_1$, L, $Z_2$, $R_1$ and $R_2$ have the same meanings as above);

$Q_1$ represents a halogen atom such as a bromine atom or an iodine atom, or $(HO)_2$—B—;

Arp represents Ar optionally having a protective group;

$P_2$ represents a hydroxyl-protective group;

X, Ar and Y have the same meanings as above.]

1-1) Production Method for Compound of Formula (IV):

A compound of a formula (II) is reacted with a compound of a formula (III) in an organic solvent in the presence of a base and in the presence of a metal catalyst to obtain a compound of a formula (IV).

The amount of the compound of formula (II) to be used may be from 0.1 mol to an excessive molar amount relative to one mol of the compound of formula (III), preferably from 0.3 mols to 5 mols.

The base includes potassium carbonate, sodium hydrogencarbonate, sodium carbonate, cesium carbonate, potassium acetate, sodium acetate, tripotassium phosphate, triethylamine, pyridine, et al.

The amount of the base to be used may be from 0.1 mol to an excessive molar amount relative to 1 mol of the compound of formula (II), preferably from 0.5 mols to 5 mols.

The metal catalyst includes copper(0), copper(I) chloride, copper(II) chloride, copper(I) bromide, copper(II) bromide, copper(I) iodide, copper(II) iodide, copper(I) acetate, copper (I) oxide, copper(II) oxide, et al, preferably copper(0), copper (I) iodide, copper(II) acetate.

The amount of the metal catalyst to be used may be from 0.01 mols to 10 moles relative to 1 mol of the compound of formula (II), preferably from 0.3 mols to 3 mols.

If desired, molecular sieves may be added to the reaction system; as molecular sieves, usable is MS-4A, and its amount to be used may be from 0.01% by weight to an excessive wt. % relative to the compound of formula (II), preferably from 0.1% by weight to 20% by weight.

The organic solvent includes, for example, methylene chloride, chloroform, tetrahydrofuran (hereinafter referred to as "THF"), 1,4-dioxane (hereinafter referred to as "dioxane"), dimethylformamide (hereinafter referred to as "DMF"), N-methylpyrrolidone (hereinafter referred to as "NMP"), dimethylsulfoxide (hereinafter referred to as "DMSO"), benzene, toluene, nitrobenzene, et al, and their mixed solvents.

The reaction temperature may be from 0° C. to 300° C., preferably from 20° C. to 200° C. In general, the reaction takes from 5 minutes to 14 days, preferably from 2 hours to 7 days.

Thus obtained, the compound of formula (IV) may be isolated and purified in any known separation and purification method, for example, concentration, concentration under reduced pressure, crystallization, solvent extraction, reprecipitation, chromatography, et al (the same shall apply to the reaction mentioned hereinunder).

1-2) Production Method for Compound of Formula (I) Through Deprotection:

The compound of formula (IV) where A is Arp-Y— and E is the formula (a) corresponds to a compound of a formula (Ip), and the compound may be converted into a compound of formula (I) optionally by removing the protective group.

Reaction Formula 2

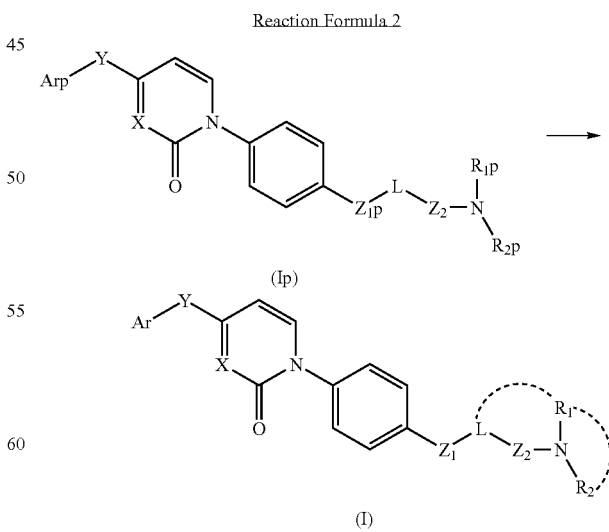

[In the formula, Arp, Y, X, $Z_1p$, L, $Z_1$, $Z_2$, $R_1p$, $R_2p$, $R_1$, $R_2$ and Ar have the same meanings as above.]

The removal of the protective group, though differing depending on the type of the protective group and the stability of the product compound, may be attained, for example, through solvolysis with acid or base, for example, according to methods described in literature [see Protective Groups in Organic Synthesis, T. W. Greene, John Wiley & Sons, 1981], or any methods according to them concretely, for example, according to a method of processing with from 0.01 mol to a large excessive amount of an acid, preferably trifluoroacetic acid, formic acid, hydrochloric acid et al, or with from an equimolar amount to a large excessive amount of a base, preferably potassium hydroxide, calcium hydroxide et al; or through chemical reduction with a metal hydride complex; or through catalytic reduction with a palladium-carbon catalyst or a Raney-nickel catalyst et al.

The protective group usable herein includes an amino group, an imino group, a hydroxyl group, a carboxyl group, an oxo group.

Having its function, the protective group for amino group and imino group is not specifically limited, and includes, for example, an aralkyl group such as a benzyl group, a p-methoxybenzyl group, a 3,4-dimethoxybenzyl group, an o-nitrobenzyl group, a p-nitrobenzyl group, a benzhydryl group, a trityl group et al; a lower alkanoyl group such as a formyl group, an acetyl group, a propionyl group, a butyryl group, a pivaloyl group et al; a benzoyl group; an arylalkanoyl group such as a phenylacetyl group, a phenoxyacetyl group et al; a lower alkoxycarbonyl group such as a methoxycarbonyl group, an ethoxycarbonyl group, a propyloxycarbonyl group, a tert-butoxycarbonyl group et al; a lower alkylsilyl group such as a trimethylsilyl group, a tert-butyldimethylsilyl group et al; a tetrahydropyranyl group; a trimethylsilylethoxymethyl group; a lower alkylsulfonyl group such as a methylsulfonyl group, an ethylsulfonyl group et al; an arylsulfonyl group such as a benzenesulfonyl group, a toluenesulfonyl group et al; and especially preferred are an acetyl group, a benzoyl group, a tert-butoxycarbonyl group, a trimethylsilylethoxymethyl group et al.

Having its function, the protective group for hydroxyl group is not specifically limited, and includes, for example, a lower alkyl group such as a methyl group, an ethyl group, a propyl group, an isopropyl group, a tert-butyl group et al; a lower alkylsilyl group such as a trimethylsilyl group, a tert-butyldimethylsilyl group et al; a lower alkoxymethyl group such as a methoxymethyl group, a 2-methoxyethoxymethyl group et al; a tetrahydropyranyl group; a trimethylsilylethoxymethyl group; an aralkyl group such as a benzyl group, a p-methoxybenzyl group, a 2,3-dimethoxybenzyl group, an o-nitrobenzyl group, a p-nitrobenzyl group, a trityl group et al; an acyl group such as a formyl group, an acetyl group et al. Especially preferred are a methyl group, a methoxymethyl group, a tetrahydropyranyl group, a trityl group, a trimethylsilylethoxymethyl group, a tert-butyldimethylsilyl group, an acetyl group et al.

Not specifically limited, the carboxyl-protective group may be any one having its function, and includes, for example, a lower alkyl group such as a methyl group, an ethyl group, a propyl group, an isopropyl group, a tert-butyl group et al; a lower haloalkyl group such as a 2,2,2-trichloroethyl group; a lower alkenyl group such as a 2-propenyl group; an aralkyl group such as a benzyl group, a p-methoxybenzyl group, a p-nitrobenzyl group, a benzhydryl group, a trityl group et al. Especially preferred are a methyl group, an ethyl group, a tert-butyl group, a 2-propenyl group, a benzyl group, a p-methoxybenzyl group, a benzhydryl group et al.

Not specifically limited, the protective group for oxo group and carbonyl group may be any one having its function, and includes, for example, acetals and ketals such as ethylene ketal, trimethylen ketal, dimethyl ketal et al.

Production Method for Compound of Formula (Ip)

In case where A is not Arp-Y— and E is any of (b) to (d) in the compound of formula (IV), a compound of a formula (Ip) may be prepared according to a process of leading A into Arp-Y— (process A) and a process of leading E to (a) (process E). In this case, the order of the process A and the process E is not limited. Specifically, the process A may be followed by the process E, and the process E may be followed by the process A. Production methods 2 to 5 are for the process E; and production methods 6 and 7 are for the process A.

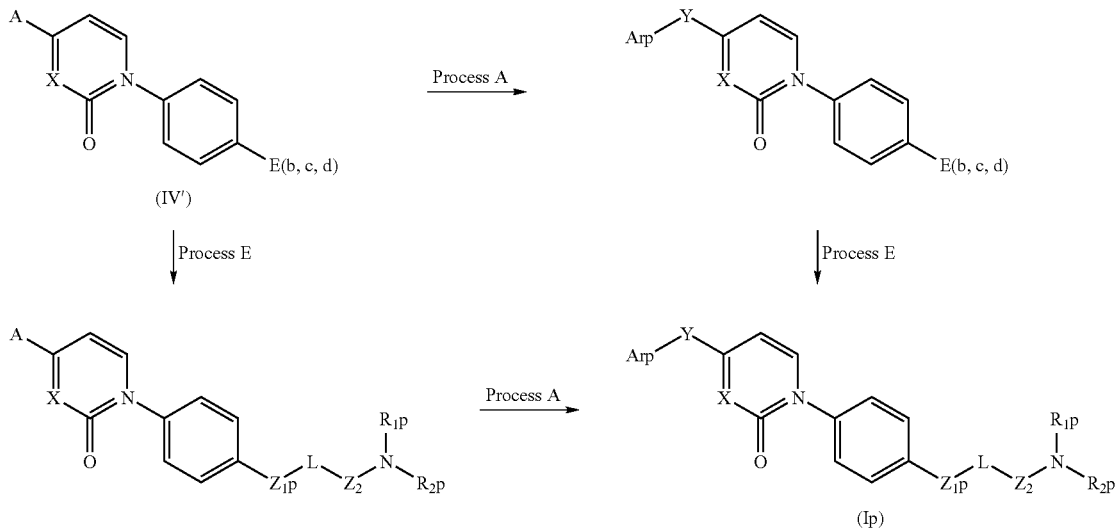

Reaction Formula 3

[In the formula, E(b,c,d) means that E is any of formula (b), formula (c) or formula (d); and A, Arp, Y, X, $Z_1p$, L, $Z_2$, $R_1p$ and $R_2p$ have the same meanings as above.]

Production Method 2:

The compound of formula (IV) where E is formula (b), or that is, a compound of a formula (IVb) may be converted into a compound of a formula (IbP) according to the production method 2. In this, when A is Arp-Y—, if desired, it may be deprotected to give a compound of formula (I).

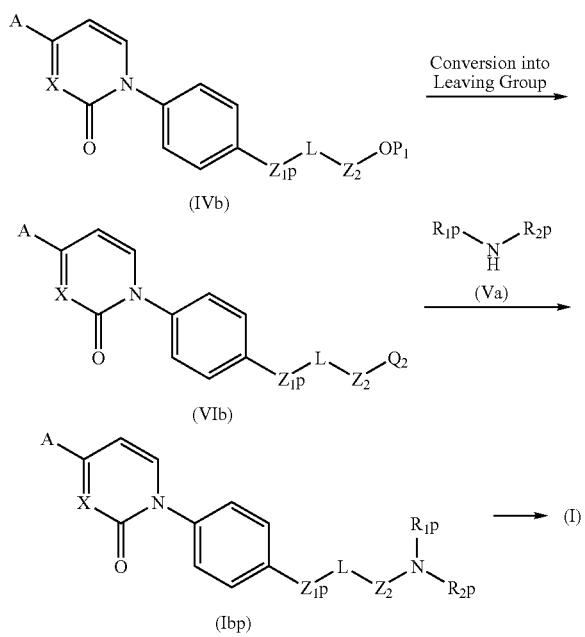

Reaction Formula 4

[In the formula, $Q_2$ represents a halogen atom such as a chlorine atom, a bromine atom, an iodine atom, or an organic sulfonyloxy group such as a methanesulfonyloxy group, a trifluoromethanesulfonyl group, a p-toluenesulfonyloxy group et al; and A, $P_1$, $R_1p$, $R_2p$, $Z_1p$, L, $Z_2$ and X have the same meanings as above.]

In case where $P_1$ in the compound of formula (IVb) is a hydrogen atom, a leaving group is introduced into the compound of formula (IVb) as such. In case where $P_1$ is a hydroxyl-protective group, the protective group $P_1$ in the compound of formula (IV) is removed, and then a leaving group is introduced to give a compound of formula (VIb).

The introduction of a leaving group into the compound of formula (IV) or into its deprotected form may be attained in a conventional known method.

Subsequently, the compound of formula (VIb) is reacted with a compound of a formula (Va) without solvent, in water, or in an organic solvent in the presence or absence of a base, to obtain a compound of a formula (Ibp).

The base includes an inorganic base such as cesium carbonate, sodium carbonate, potassium carbonate, sodium hydroxide, potassium hydroxide, sodium hydrogencarbonate, potassium hydrogencarbonate et al.

The amount of the base to be used may be from 1 mol to an excessive molar amount relative to 1 mol of the compound of formula (Va), preferably from 2 mols to 10 mols.

The amount of the compound of formula (Va) to be used may be from 1 mol to an excessive molar amount relative to 1 mol of the compound of formula (VIb), preferably from 5 mols to 20 mols.

The organic solvent includes halogenocarbons such as methylene chloride, chloroform, dichloroethane, carbon tetrachloride et al; aliphatic hydrocarbons such as n-heptane, n-hexane et al; aromatic hydrocarbons such as benzene, toluene, xylene et al; ethers such as diethyl ether, THF, dioxane, ethylene glycol dimethyl ether et al; acetonitrile, NMP, DMF, DMSO; alcohols such as ethanol, methanol, t-butanol et al; their mixed solvents; and their mixed solvent with water.

The reaction temperature may be from 0° C. to 200° C., preferably from 20° C. to 150° C., and in general, the reaction takes 30 minutes to 12 hours.

The compound of formula (Va) includes, for example, dimethylamine, diethylamine, di-n-propylamine, N-ethylmethylamine, N-methyl-n-propylamine, N-methylisopropylamine, N-methyl-n-butylamine, N-ethyl-n-propylamine, N-ethylisopropylamine, aziridine, pyrrolidine, piperidine, N-methylpiperazine, morpholine, methylamine, ethylamine, n-propylamine, isopropylamine, cyclopropylamine, n-butylamine, sec-butylamine, tert-butylamine, cyclopropanemethylamine, benzylamine, methyl(pyridin-2-ylmethyl)amine et al.

Production Method 3:

The compound of formula (IV) where E is formula (c), or that is, a compound of a formula (IVc) may be converted into a compound of a formula (Icp) according to Production Method 3. In case where A in formula (Icp) is Arp-Y—, if desired, it may be deprotected to give a compound of a formula (Ic).

Reaction Formula 5

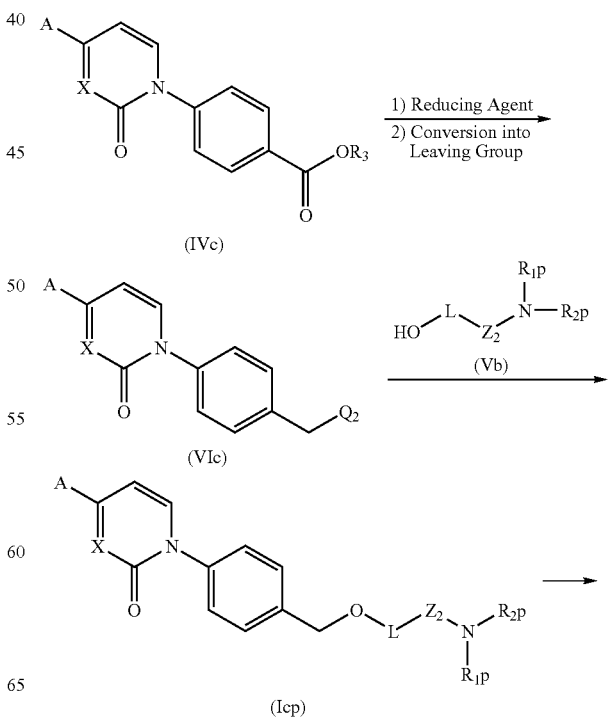

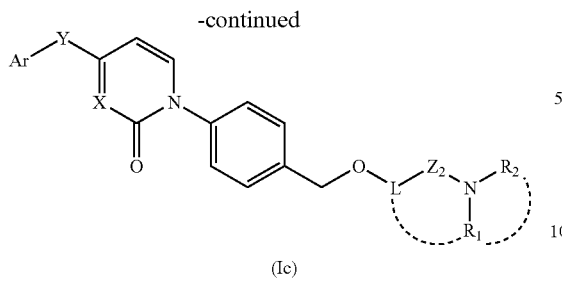

(Ic)

[In the formula, A, X, $Q_2$, $R_1p$, $R_2p$, L, $Z_2$, $R_1$, $R_2$, $R_3$, Ar and Y have the same meanings as above.]

The ester moiety in the compound of formula (IVc) is reduced according to a known method using a reducing agent such as lithiumaluminium hydride (hereinafter referred to as "LAH"), lithium borohydride, diisobutylaluminium hydride et al, then the formed hydroxyl group is converted into a leaving group ($Q_2$) such as a halogen, a methanesulfonyloxy group, a p-toluenesulfonyloxy group et al, thereby giving a compound of a formula (VIc).

Subsequently, the compound of formula (VIc) is condensed with a compound of a formula (Vb) in an organic solvent in the presence of a base to obtain a compound of a formula (Icp).

The amount of the compound of formula (Vb) to be used may be from 1 to 10 mols relative to 1 mol of the compound of formula (VIc), preferably from 1 to 3 mols.

The base includes, for example, sodium hydride, potassium hydride, sodium t-butoxide, potassium t-butoxide et al, preferably sodium hydride, potassium t-butoxide et al.

The amount of the base to be used may be from 1 to 10 mols relative to 1 mol of the compound of formula (VIc), preferably from 1 to 3 mols.

The organic solvent includes, for example, diethyl ether, dioxane, THF, DMF, DMSO et al.

The reaction time may be form 5 minutes to 3 days, preferably from 30 minutes to 24 hours; and in general, the reaction takes from 2 hours to 24 hours.

In case where A in the compound of formula (Icp) is Arp-Y— and the substituent has a protective group, then the protective group is removed to obtain a compound of formula (Ic).

Production Method 4:

Production method 4 is a production for a compound of formula (I) where $Z_1$ corresponds to NR, or that is, a compound of a formula (Ic'). For example, starting from a compound of formula (IVc), a compound of formula (Ic') shall be produced.

Specifically, in case where $R_3$ is a hydrogen atom in the compound of formula (IVc), the carboxylic acid (IVc') is subjected to Curtius rearrangement to obtain a compound of a formula (VIIc), then the compound of formula (VIIc) is condensed with a compound of a formula (Vc) and then processed in several process to give a compound of a formula (Ic').

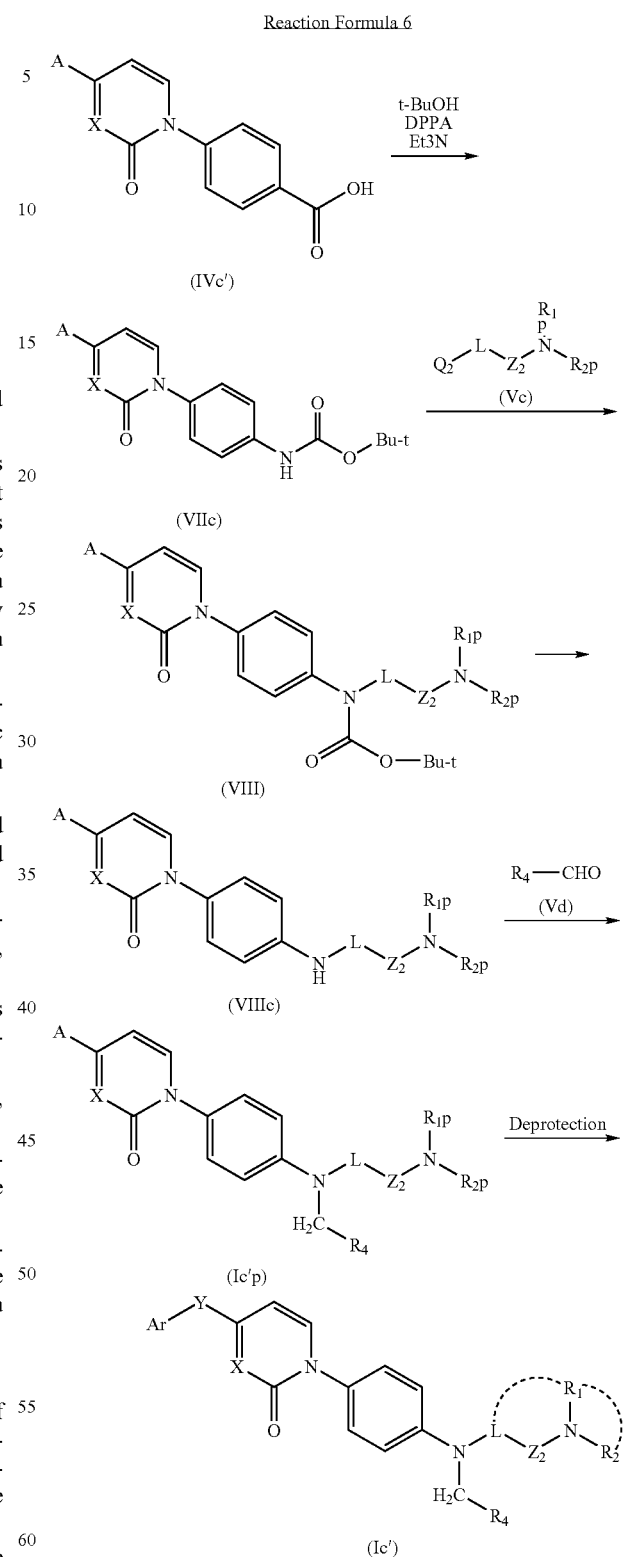

[In the formula, $R_4$ represents a group of which $CH_2$ residue is removing from R when R is a lower alkyl; and A, $Q_2$, $R_1p$, $R_2p$, Y, L, $Z_2$, X, $R_1$, $R_2$, R and Ar have the same meanings as above.]

Specifically, the ester moiety in a compound of a formula (IVc) is hydrolyzed to give a compound of a formula (IVc'), then the compound of formula (IVc') is subjected to Curtius rearrangement to obtain a compound of a formula (VIIc).

Concretely, a compound of formula (IVc') is reacted with diphenylphosphorylazide (DPPA) in t-butanol under heated in the presence of triethylamine ($Et_3N$) to give a compound of formula (VIIc) via an acylazide and via an isocyanate intermediate. For the reaction condition, referred to is Tetrahedron, Vol. 30, p. 2151, 1974.

Subsequently, the compound of formula (VIIc) is treated with a compound of a formula (Vc) in an organic solvent in the presence of a base according to the production method 3 to give a compound of a formula (VIII).

Subsequently, the compound of formula (VIII) is treated with trifluoroacetic acid (hereinafter referred to as "TFA") to remove the Boc group to give a compound of a formula (VIIIc).

For the method of removing the protective group, referred to is Protective Groups in Organic Synthesis.

Next, the compound of formula (VIIIc) is optionally reductive alkylated with a compound of a formula (Vd) to give a compound of a formula (Ic'p).

The amount of the compound of formula (VIIIc) and the compound of formula (Vd) to be used may be generally such that the two are used both in an equimolar amount or any one is used in a small excessive molar amount.

The reaction may be attained generally in an inert solvent not having any negative influence on the reaction. The inert solvent includes, for example, alcohols such as methanol, ethanol et al; ethers such as diethyl ether, THF, dioxane et al; aromatic hydrocarbons such as benzene, toluene et al; halogenohydrocarbons such as methylene chloride, chloroform, carbon tetrachloride, dichloroethane, trichloroethylene et al; and their mixed solvents.

The reaction may be attained in the presence of a metal hydride complex such as sodium borohydride, sodium cyanoborohydride, lithiumaluminium hydride, sodium triacetoxyborohydride et al, or through catalytic reduction using, for example, a palladium-carbon catalyst or a Raney nickel catalyst et al; and in particular, preferred is using a metal hydride complex such as sodium borohydride, sodium cyanoborohydride, or sodium triacetoxyborohydride et al.

The reaction is preferably attained under a weak acidic condition under which a Schiff base is easily formed. In case where the reduction is attained in the condition, it is desirable to use sodium cyanoborohydride, zinc cyanoborohydride or sodium triacetoxyborohydride that is relatively stable in acid.

In case where a metal hydride complex is used as the reducing agent, the amount of the reducing agent to be used may be generally from 1 mol to an excessive molar amount relative to 1 mol of the compound of formula (VIIIc), preferably from 1 mol to 10 mols.

The acid usable for pH control for attaining the weak acidic condition for Schiff base formation includes, for example, p-toluenesulfonic acid, hydrochloric acid, acetic acid, trifluoroacetic acid et al.

The reaction temperature may be generally from about −30° C. to about 200° C., preferably from about 0° C. to about 100° C.; and the reaction time may be generally from 10 minutes to 7 days, preferably from 10 minutes to 24 hours.

The hydrogen pressure in catalytic reduction is generally preferably from normal pressure to 5 atmospheres; and the amount of the catalyst to be used may be generally from 1 to 100% by weight relative to the compound of formula (VIIIc), preferably from 1 to 10% by weight.

In case where A in the compound of formula (Ic'p) is Arp-Y— and the substituent has a protective group, the protective group may be removed to give a compound of a formula (Ic').

Production Method 5:

The compound of formula (IV) where E is formula (d), or that is, a compound of a formula (IVd) may be converted into a compound of a formula (Idp) according to Production Method 5. In this, when A is Arp-Y—, if desired, the protective group may be removed to give a compound of a formula (Id).

Reaction Formula 7

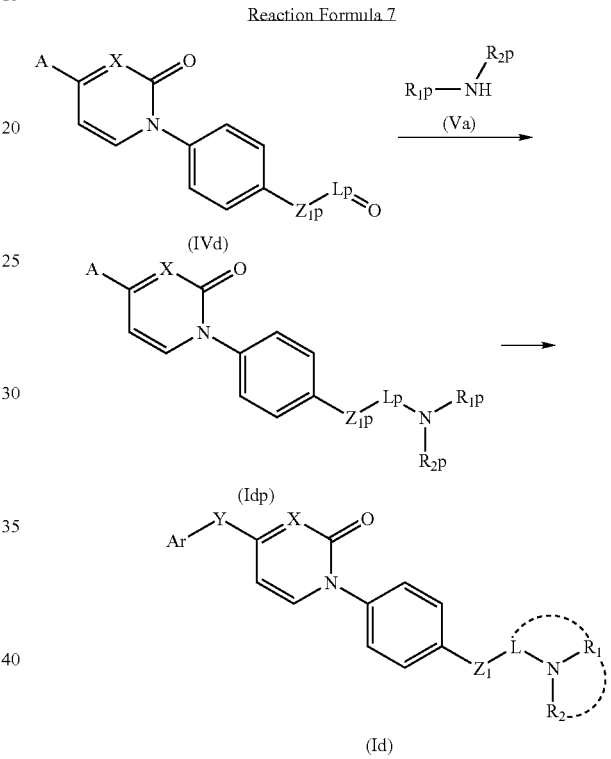

[In the formula, A, X, $Z_1p$, Lp, $R_1p$, $R_2p$, $R_1$, $R_2$, $Z_1$, L, Ar and Y have the same meanings as above.]

A compound of a formula (IVd) is reacted with a compound of a formula (Va) for reductive alkylation to give a compound of a formula (Idp). In case where A in the compound of formula (Idp) is Arp-Y— and the substituent has a protective group, the protective group may be removed to give a compound of a formula (Id).

The reaction of the compound of formula (IVd) and the compound of formula (Va) may be attained according to the method of reductive alkylation of the production method 4. The removal of the protective group may also be attained according to the above-mentioned method.

Production Method 6:

The compound of formula (IV) where A is $P_2$—O—, or that is, a compound of a formula (IVe) may be converted into a compound of a formula (Iep) according to Production Method 6. In this when E is formula (a), then if desired, it may be deprotected to give a compound of a formula (Ie).

Reaction Formula 8

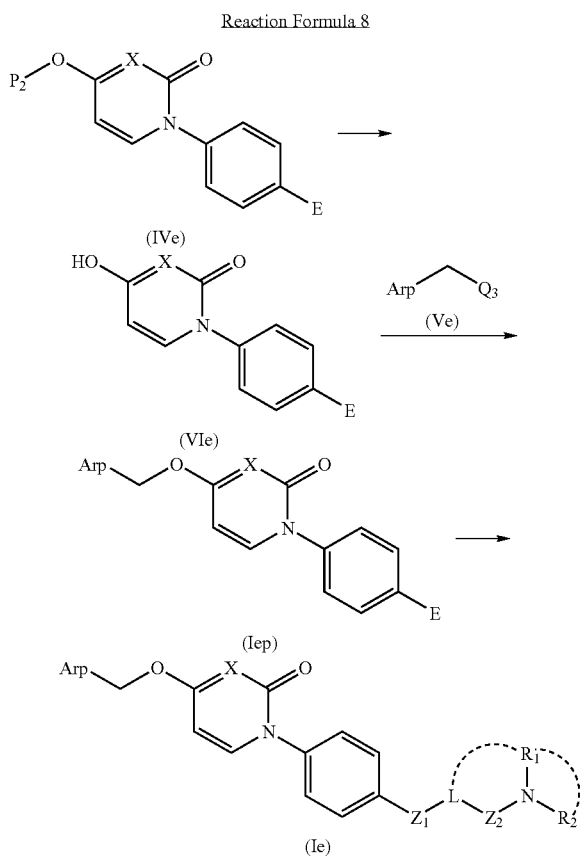

[In the formula, $Q_3$ represents a hydroxyl group or $Q_2$; and Arp, $P_2$, X, $Z_1$, L, $Z_2$, $R_1$, $R_2$, Ar, E and $Q_2$ have the same meanings as above.]

The protective group $P_2$ in the compound of formula (IVe) is removed to give a compound of a formula (VIe). Subsequently, the compound of formula (VIe) is condensed with a compound of a formula (Ve) according to the following methods, depending on the type of the compound of formula (Ve).

1) In Case where $Q_3$ is a Hydroxyl Group:

A compound of formula (VIe) is condensed with a compound of formula (Ve) through Mitsunobu reaction to give a compound of a formula (Iep). Then, in case where E in formula (Iep) is (a) and the substituent has a protective group, the protective group may be removed to give a compound of a formula (Ie).

The condensation of the compound of formula (VIe) with the compound of formula (Ve) may be attained in a reaction solvent in the presence of an azodicarbonyl compound and an organophosphorus compound such as triaryl phosphine or trialkyl phosphine, thereby giving a compound of formula (Iep).

The azodicarbonyl compound includes dimethyl azodicarboxylate, diethyl azodicarboxylate, diisopropyl azodicarboxylate, di-t-butyl azodicarboxylate, 1,1'-(azodicarbonyl)dipiperidide et al; the triaryl phosphine includes triphenyl phosphine, tritolyl phosphine et al; the trialkyl phosphine includes triethyl phosphine, tributyl phosphine, trioctyl phosphine et al. Above all, recommended is a combination of diisopropyl azodicarboxylate and triphenyl phosphine, or a combination of 1,1'-(azodicarbonyl)dipiperidide and tributyl phosphine.

The amount of the compound of formula (Ve) to be used may be from 1 mol to 3 mol relative to 1 mol of the compound of formula (VIe) preferably from 1 mol to 1.5 mols.

Regarding the amount of the azodicarbonyl compound and the organophosphorus compound such as triaryl phosphine or trialkyl phosphine to be used, the amount of the azodicarbonyl compound may be from 1 mol to 3 mols relative to 1 mol of the compound of formula (VIe), preferably from 1 mol to 1.5 mols, and the amount of the organophosphorus compound may be from 1 mol to 3 mols relative to one mol of the compound of formula (VIe), preferably from 1 mol to 1.5 mols.

The reaction solvent includes halogenocarbons such as methylene chloride, chloroform, dichloroethane, carbon tetrachloride et al; aliphatic hydrocarbons such as n-heptane, n-hexane et al; aromatic hydrocarbons such as benzene, toluene, xylene et al; ethers such as diethyl ether, THF, dioxane, ethylene glycol dimethyl ether et al; esters such as methyl acetate, ethyl acetate et al; acetonitrile, NMP, DMF, DMSO et al; and their mixed solvents.

The reaction temperature may be from 0° C. to 100° C., preferably from 0° C. to 50° C.; and in general, the reaction takes 2 hours to 24 hours.

2) In Case where $Q_3$ has the Same Meaning as $Q_2$:

A compound of formula (IVe) is condensed with a compound of formula (Ve) in an organic solvent, preferably in the presence of a base to give a compound of formula (Iep).

The reaction condition may be the same as that for the alkylation in the production method 2.

Production Method 7:

The compound of formula (IV) where the moiety of A has a double bond, or that is, a compound of a formula (VIf) may be prepared according to the following method starting from a compound of formula (II) where A is a methyl group, or that is, a compound of a formula (IX).

Reaction Formula 9

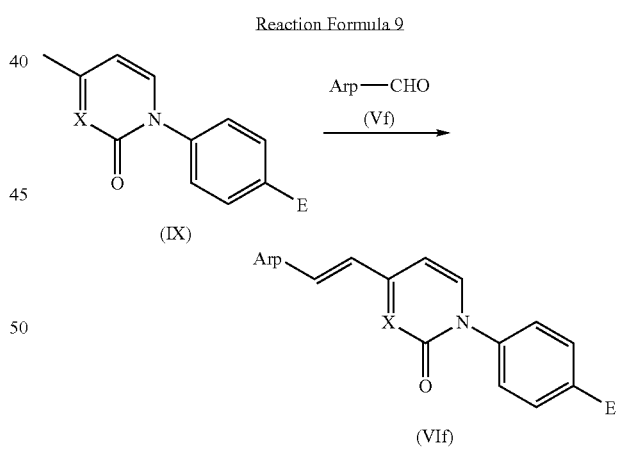

[In the formula, Arp, X and E have the same meanings as above.]

Specifically, in an organic solvent, a compound of formula (IX) is condensed with a compound of formula (Vf) in the presence of a base to give a compound of a formula (VIf).

The amount of the compound of formula (Vf) to be used may be from 1 to 20 mols relative to 1 mol of the compound of formula (IX), preferably from 1 to 3 mols.

The base includes sodium hydride, sodium hydroxide, potassium carbonate, sodium carbonate et al, preferably sodium hydride, sodium hydroxide et al.

The amount of the base to be used may be from 0.01 to 10 mols relative to 1 mol of the compound of formula (IX), preferably from 0.1 to 2 mols.

The organic solvent includes ethers such as diethyl ether, THF, dioxane et al; DMF, DMSO et al.

The reaction temperature may be from −20 to 100° C., preferably from 0 to 50° C.; and in general, the reaction takes 0.1 to 24 hours.

In the above-mentioned production methods, the compound of formula (II), the compound of formula (III), the compound of formula (Va), the compound of formula (Vb), the compound of formula (Vc), the compound of formula (Vd), the compound of formula (Ve) and the compound of formula (Vf) may be commercial products, or may be prepared according to the methods described in Examples or Reference Examples or according to known methods. The compound of formula (IX) may be prepared according to the production method 1.

The compounds of formula (I) obtained according to the above-mentioned methods may be readily isolated and purified in any conventional known separation method. The method includes, for example, solvent extraction, recrystallization, column chromatography, liquid chromatography, or preparative thin-layer chromatography et al.

Depending on the type of the substituent therein, the compounds of the invention may be in any form of stereoisomers and tautomers such as optical isomers, diastereomers, geometrical isomers et al; and the compounds of the invention include all those stereoisomers and tautomers and their mixtures.

Pharmacological Test of the Compounds of Formula (I)

The usefulness of the compounds of the invention as medicines is showed, for example, by the following pharmacological test example.

Pharmacological Test Example 1 (MCH Binding Inhibition Test)

A human MCH-1R encoding cDNA sequence [FEBS Letters, Vol. 398, 253 (1996); Biochimica et Biophisica Acta, Vol. 1401, 216 (1998)] was cloned to a plasmid vector pEF/myc/cyto (Invitrogen Corporation). The obtained expression vector was transfected to host cells CHO-K1 (American Type Culture Collection) using Lipofectamine Plus Reagent (Life Technology Inc.) to provide MCH-1R expression cells.

Membrane samples prepared from the MCH-1R expression cells were incubated with each test compound and 50 pM of [$^{125}$I]MCH (NEN Co.), in an assay buffer (50 mM Tris buffer comprising 10 mM magnesium chloride, 2 mM ethylenediamine tetraacetate, 0.01% bacitracin and 0.2% bovine serum albumin; pH 7.4) at 25° C. for an hour, followed by filtration through a glass filter GF/C (Wattman Co.). After washing the glass filter with 50 mM Tris buffer (pH 7.4) comprising 10 mM magnesium chloride, 2 mM ethylenediamine tetraacetate and 0.04% Tween-20, the radioactive activity on the glass filter was measured. The non-specific binding was measured in the presence of 1 μM human MCH and 50% inhibition concentration ($IC_{50}$ value) of each test compound to the specific [$^{125}$I]MCH binding was determined. The results are shown in Table 1.

TABLE 1

| Compound of Example | IC50 (nM) |
|---|---|
| 3 | 1.5 |
| 4 | 1.2 |
| 5 | 1.4 |
| 6 | 0.93 |
| 8 | 1.4 |
| 14 | 4.5 |
| 27 | 5.8 |
| 32 | 6.2 |
| 37 | 4.6 |
| 53 | 3.5 |

The compounds of the invention has an MCH-1R antagonistic effect, and are useful as a preventive or a remedy for metabolic disorders such as obesity, diabetes, hormone disorder, hyperlipidemia, gout, fatty liver, hepatitis, cirrhosis; cardiovascular disorders such as stenocardia, acute or congestive heart failure, myocardial infarction, coronary atherosclerosis, hypertension, renal diseases, electrolyte abnormality; central and peripheral nervous system disorders such as bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence, alcoholism; reproductive disorders such as infertility, preterm labor and sexual dysfunction; and other digestive disorders, respiratory disorders, cancer or pigmentation et al; especially as a preventive or a remedy for obesity.

Pharmaceutical Composition Comprising the Compound of the Invention

The compound of the invention can be orally or parenterally administered, and can be formulated into preparations suitable to the administration thereof, which may be used as a preventive or a remedy for metabolic disorders such as obesity, diabetes, hormone disorder, hyperlipidemia, gout, fatty liver, hepatitis, cirrhosis; cardiovascular disorders such as stenocardia, acute or congestive heart failure, myocardial infarction, coronary atherosclerosis, hypertension, renal diseases, electrolyte abnormality; central and peripheral nervous system disorders such as bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence, alcoholism; reproductive disorders such as infertility, preterm labor and sexual dysfunction; and other digestive disorders, respiratory disorders, cancer or pigmentation et al; especially as a preventive or a remedy for obesity.

In its clinical use, the compound of the invention may be formulated into various preparations along with a pharmaceutically-acceptable carrier added thereto generally in accordance with the administration route thereof, and the thus-formulated pharmaceutical composition may be administered. As the carriers, usable are various conventional additives known in the field of pharmaceutical preparations. For example, they include gelatin, lactose, white sugar, titanium oxide, starch, crystalline cellulose, hydroxypropylmethyl cellulose, carboxymethyl cellulose, corn starch, microcrystalline wax, white petrolatum, magnesium aluminate metasilicate, anhydrous calcium phosphate, citric acid, trisodium citrate, hydroxypropyl cellulose, sorbitol, sorbitan fatty acid esters, polysorbate, sucrose fatty acid esters, polyoxyethylene, hardened castor oil, polyvinylpyrrolidone, magnesium stearate, light silicic anhydride, talc, vegetable oils, benzyl alcohol, gum arabic, propylene glycol, polyalkylene glycol, cyclodextrin and hydroxypropylcyclodextrin et al.

Preparations to be formed as a mixture of the carrier and a compound of the invention include, for example, solid preparations such as tablets, capsules, granules, powders and suppositories et al; and liquid preparations such as syrups, elixirs and injections et al. These may be formulated according to conventional methods known in the field of pharmaceutical preparations. The liquid preparations may also be in such a form that may be dissolved or suspended in water or in any other suitable medium in their use. Especially for injections, if desired, the preparations may be dissolved or suspended in physiological saline water or glucose liquid, and a buffer or a preservative may be optionally added thereto.

The pharmaceutical compositions may contain a compound of the invention in an amount of from 1.0 to 100% by weight, preferably from 1.0 to 60% by weight of the composition, and may contain a pharmaceutically-acceptable carrier in an amount of from 0 to 99.0% by weight, preferably from 40 to 99.0% by weight. The compositions may further contain any other therapeutically-effective compound, for example, a remedy for diabetes, a remedy for hypertension, a remedy for arteriosclerosis.

In case where the compounds of the invention are used for prevention, treatment or remedy of the above-mentioned diseases or disorders, then the dose and the dosing frequency may be varied, depending on the sex, the age, the body weight and the disease condition of the patient and on the type and the range of the intended remedial effect. In general, the dose may be from 0.001 to 50 mg/kg of body weight/day, and it may be administered at a time or in a few times. The dose is preferably from about 0.01 to about 25 mg/kg/day, more preferably from about 0.05 to about 10 mg/kg/day.

Combination Therapy Using Compound of the Invention

The compounds of the invention can be used in combination with drugs effective for hypertension, obesity-associated hypertension, hypertension-associated diseases, hypertrophy, left ventricular hypertrophy, metabolic disorders, obesity, obesity-associated diseases and the like (hereafter referred to as "co-drugs"). Such drugs can be administered simultaneously, separately or in succession, for prevention or treatment of the above-mentioned diseases. When a compound of the invention is used simultaneously with one, two or more of co-drugs, they may be formulated into a medical preparation suited for single administration form. Whereas, in combination therapy, a composition containing a compound of the invention and a co-drug may be administered to the object of medication in different packages, either simultaneously, separately or successively. They may be administered at time intervals.

The dose of the co-drug may be determined in accordance with the clinically adopted dose thereof, which can be suitably selected according to the individual object of medication, the administration route, the specific disease, the combination of drugs, and the like. The form of the co-drug for administration is not specifically limited, it may be combined with a compound of the invention when they are administered. The administration mode includes, for example, the following: (1) A compound of the invention is simultaneously formulated with a co-drug to give a single preparation for single administration; (2) a compound of the invention and a co-drug are separately formulated into different two preparations, and the two preparations are simultaneously administered in one administration route; (3) a compound of the invention and a co-drug are separately formulated into different two preparations, and they are administered at different times in one and the same administration route; (4) a compound of the invention and a co-drug are separately formulated into different two preparations, and they are administered at the same time in two different administration routes; (5) a compound of the invention and a co-drug are separately formulated into different two preparations, and they are administered at different times in different administration routes (for example, a compound of the invention and a co-drug are administered in that order, or in an order contrary to this). The blend ratio of the compound of the invention and the co-drug may be suitably determined depending on the administration object, the administration route, and the disease for the administration.

The co-drugs usable in the invention include, for example, "drugs for diabetes", "drugs for hyperlipidemia", "drugs for hypertension", "anti-obesity drugs". Two or more such co-drugs may be combined in an adequate ratio and used.

"Drugs for diabetes" include, for example,

1) PPAR-γ agonists such as glitazones (e.g., ciglitazone, darglitazone, englitazone, isaglitazone, (MCC-555) et al), pioglitazone, rosiglitazone, troglitazone, BRL49653, CLX-0921, 5-BTZD, GW-0207, LG-100641, LY-300512 et al;
2) biguanides such as metformin, buformin, phenformin et al;
3) protein tyrosine phosphatase 1B inhibitors;
4) sulfonylureas such as acetohexamide, chloropropamide, diabinese, glibenclamide, glipizide, glyburide, glimepiride, gliclazide, glipentide, gliquidone, glisolamide, trazamide, tolubutamide et al;
5) meglitinides such as repaglinide, nateglinide et al;
6) α-glucoside hydroxylase inhibitors such as acarbose, adiposine, camiglibose, emiglitate, miglitol, voglibose, pradimicin-Q, salbostatin, CKD-711, MDL-25, 673, MDL-73, 945, MOR14 et al;
7) α-amylase inhibitors such as tendamistat, trestatin, A13688 et al;
8) insulin secretion promoters such as linogliride, A-4166 et al;
9) fatty acid oxidation inhibitors such as clomoxir, etomoxir et al;
10) A2 antagonists such as midaglizole, isaglidole, deriglidole, idazoxan, earoxan, fluparoxan et al;
11) insulin or insulin mimetics such as biota, LP-100, novalapid, insulin determir, insulin lispro, insulin glargine, insulin zinc, Lys-Pro-insulin, GLP-1 (73-7), GLP1 amide (7-36) et al;
12) non-thiazolidinediones such as JT-501, farglitazar et al;
13) PPARα/γ dual-agonists such as MK-0767, CLX-0940, GW-1536, GW-1929, GW-2433, KRP-297, L-796449, LR-90 and SB219994 et al.

"Drugs for hyperlipidemia" include, for example, 1) bile acid absorption promoters such as cholesterylamine, colesevelem, colestipol, crosslinked dextran dialkylaminoalkyl derivatives, Colestid™, LoCholest™, Questran™ et al;
2) HMG-CoA reductase inhibitors such as atorvastatin, itavastatin, fluvastatin, lovastatin, pravastatin, rivastatin, rosuvastatin, simvastatin, ZD-4522 et al;
3) HMG-CoA synthase inhibitors;
4) cholesterol absorption inhibitors such as snatol ester, β-sitosterol, sterol glucoside, ezetimibe et al;
5) acyl-coenzyme A cholesterol acyl transferase inhibitors such as avasimibe, eflucimibe, KY-505, SMP-709 et al;
6) CETP inhibitors such as JTT705, torcetrapib, CP532632, BAY-63-2149, SC-591, SC-795 et al;
7) squalane synthetase inhibitors;
8) antioxidants such as probucol;

9) PPAR-α agonists such as beclofibrate, benzafibrate, syprofibrate, clofibrate, etofibrate, fenofibrate, gemcabene, gemfibrozil, GW-7647, BM-170744, LY-518674, fibric acid derivatives (e.g., Atromid™, Lopid™, Tricor™) et al;
10) FXR receptor antagonists such as GW-4064, SR-103912 et al;
11) LXR receptor agonists such as GW3965, T9013137, XTCO-179628 et al;
12) lipoprotein synthesis inhibitors such as niacin;
13) renin-angiotensin system inhibitors;
14) microsome-triglyceride transport inhibitors;
15) bile acid resorption inhibitors such as BARA1453, SC435, PHA384640, S-435, AZD7706 et al;
16) PPAR-δ agonists such as GW501516, GW590735;
17) triglyceride synthesis inhibitors;
18) MTTP inhibitors such as LAB687, CP346086;
19) low-density lipoprotein receptor inducers;
20) squalane epoxidase inhibitors;
21) thrombocyte agglutination inhibitors;
22) 5-lipoxygenase activated protein inhibitors such as MK-591.

"Drugs for hypertension" include, for example,
1) thiazide diuretics such as chlorothialidon, chlorothiazide, dichlorofenamide, hydrofluorothiazide, indapamide, hydrochlorothiazide et al; loop diuretics such as bumetanide, ethacrynic acid, flosemide, tolusemide et al; sodium diuretics such as amyloride, triamuteren et al; aldosterone antagonist diuretics such as spironolactone, epilenone et al;
2) β-adrenaline blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tartatolol, tilisolol, timolol et al;
3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, verapamil et al;
4) angiotensin converting enzyme inhibitors such as benazepril, captopril, cilazapril, delapril, enalapril, fosinopril, imidapril, rosinopril, moexipril, quinapril, quinaprilat, ramipril, perindopril, perindropril, quanipril, spirapril, tenocapril, trandolapril, zofenopril et al;
5) neutral endopeptidase inhibitors such as omapatrilat, cadoxatril, ecadotril, fosidotril, sampatrilat, AVE7688, ER4030 et al;
6) endothelin antagonists such as tezosentan, A308165, YM62899 et al;
7) vasodilators such as hydraladine, clonidine, minoxidil, nicotinyl alcohol et al;
8) angiotensin II antagonists such as candesartan, eporsartan, iribesartan, losartan, pratosartan, tasosartan, telmisartan, valsartan, EXP-3137, F16828K, RNH6270 et al;
9) α/β adrenaline blockers such as nipradilol, arotinolol, amoslalol et al;
10) α1 blockers such as terazosin, urapidil, purazosin, bunazosin, trimazosin, doxazosin, naphthopidil, indolamin, WHIP164, XEN010 et al;
11) α2 agonists such as lofexidine, tiamenidine, moxonidine, rilmenidine, guanobenz et al;
12) aldosterone inhibitors.

"Anti-obesity drugs" include, for example,
1) 5HT (serotonin) transporter inhibitors such as paroxetine, fluoxetine, fenfluramine, fluvoxamine, sertraline, imipramine et al;
2) norepinephrine transporter inhibitors such as GW320659, desipramine, talsupram, nomifensin et al;
3) cannabinoid-1 receptor 1 (CB-1) antagonists/inverse-agonists such as rimonabant (Sanofi Synthelabo), SR-147778 (Sanofi Synthelabo), BAY-65-2520 (Bayer), SLV-319 (Solvay), as well as compounds disclosed in U.S. Pat. No. 5,532,237, U.S. Pat. No. 4,973,587, U.S. Pat. No. 5,013,837, U.S. Pat. No. 5,081,122, U.S. Pat. No. 5,112,820, U.S. Pat. No. 5,292,736, U.S. Pat. No. 5,624,941, U.S. Pat. No. 6,028,084, WO96/33159, WO98/33765, WO98/43636, WO98/43635, WO01/09120, WO01/96330, WO98/31227, WO98/41519, WO98/37061, WO00/10967, WO00/10968, WO97/29079, WO99/02499, WO01/58869, WO02/076949, WO01/64632, WO01/64633, WO01/64634, WO03/006007, WO03/007887, and EP-658546 et al;
4) ghrelin antagonists such as compounds disclosed in WO01/87355, WO02/08250 et al;
5) histamine(H3) antagonists/inverse-agonists such as thioperamide, 3-(1H-imidazol-4-yl)propyl N-(pentenyl)carbonate, clobenpropit, iodofenpropit, imoproxyfen, GT2395, A331440, compounds disclosed in WO02/15905, O-[3-(1H-imidazol-4-yl)propanol]carbamate, piperazine-containing H3-receptor antagonists (Lazewska, D. et al., Pharmazie, 56: 927-32 (2001)), benzophenone derivatives (Sasse, A. et al., Arch. Pharm. (Weinheim) 334: 45-52 (2001)), substituted N-phenylcarbamates (Reidemeister, S. et al., Pharmazie, 55: 83-6 (2000)), proxyfen derivatives (Sasse, A. et al., J. Med. Chem., 43: 3335-43 (2000)) et al;
6) MCH-1R antagonists such as T-226296 (Takeda), SNP-7941 (Synaptic), other compounds disclosed in WO01/82925, WO01/87834, WO02/051809, WO02/06245, WO02/076929, WO02/076947, WO02/04433, WO02/083134, WO02/094799, WO03/004027, and JP-A-2001-226269 et al;
7) MCH-2R agonists/antagonists;
8) NPY1 antagonists such as isopropyl 3-chloro-5-(1-(6-[2-(5-ethyl-4-methyl-thiazol-2-yl)-ethyl]-4-morpholinyl-4-yl-piridin-2-ylamino)-ethyl)phenyl]carbamate, BIBP3226, BIBO3304, LY-357897, CP-671906, GI-264879, and other compounds disclosed in U.S. Pat. No. 6,001,836, WO96/14307, WO01/23387, WO99/51600, WO01/85690, WO01/85098, WO01/85173, and WO01/89528 et al;
9) NPY5 antagonists such as 152804, GW-569180A, GW-594884A, GW-587081X, GW-548118X, FR235,208, FR226928, FR240662, FR252384, 1229U91, GI-264879A, CGP71683A, LY-377897, LY366377, PD-160170, SR-120562A, SR-120819A, JCF-104, H409/22, and other compounds disclosed in U.S. Pat. No. 6,140,354, U.S. Pat. No. 6,191,160, U.S. Pat. No. 6,258,837, U.S. Pat. No. 6,313,298, U.S. Pat. No. 6,337,332, U.S. Pat. No. 6,329,395, U.S. Pat. No. 340,683, U.S. Pat. No. 6,326,375, U.S. Pat. No. 6,329,395, U.S. Pat. No. 6,337,332, U.S. Pat. No. 6,335,345, EP-01010691, EP-01044970, WO97/19682, WO97/20820, WO97/20821, WO97/20822, WO97/20823, WO98/27063, WO00/107409, WO00/185714, WO00/185730, WO00/64880, WO00/68197, WO00/69849, WO01/09120, WO01/14376, WO01/85714, WO1/85730, WO01/07409, WO01/02379, WO01/23388, WO01/23389, WO01/44201, WO01/62737, WO01/62738, WO02/20488, WO02/22592, WO02/

48152, WO02/49648, WO02/094789, and compounds disclosed in Norman et al., J. Med. Chem., 43:4288-4312 (2000) et al;
10) leptins such as human recombinant leptin (PEG-OB, Hoffman La Roche), recombinant methionylleptin (Amgen);
11) leptin derivatives such as compounds disclosed in U.S. Pat. No. 5,552,524, U.S. Pat. No. 5,552,523, U.S. Pat. No. 5,552,522, U.S. Pat. No. 5,521,283, WO96/23513, WO96/23514, WO96/23515, WO96/23516, WO96/23517, WO96/23518, WO96/23519, and WO96/23520 et al;
12) opioid antagonists such as nalmefen (Revex™), 3-methoxynaltorexone, naloxone, naltorexone, compounds disclosed in WO00/21509 et al;
13) orexin antagonists such as SB-334867A, and other compounds disclosed in WO01/96302, WO01/68609, WO02/51232, WO02/51838, and WO03/023561 et al;
14) bonbesin receptor subtype-3 agonists;
15) cholecystokinin A (CCK-A) agonists such as AR-R15849, GI-181771, JMV-180, A-71378, A-71623, SR-146131, and other compounds disclosed in U.S. Pat. No. 5,739,106 et al;
16) CNTF (ciliary neurotrophic factors) such as GI-181771 (Glaxo-Smith Kline), SR146131 (Sanofi Synthelabo), butabindide, PD170,292, PD149164 (Pfizer) et al;
17) CNTF derivatives such as axokine (Regeneron), and other compounds disclosed in WO94/09134, WO98/22128, WO99/43813 et al;
18) growth hormone secretion receptor agonists such as NN703, hexarelin, MK-0677, SM-130686, CP-424,391, L-692,429, L-163,255, and compounds disclosed in U.S. Pat. No. 6,358,951, US Patent Application Nos. 2002/049196, 2002/022637, WO01/56592, WO02/32888 et al;
19) serotonin receptor-2C agonists such as BVT933, DPCA37215, IK264, PNU22394, WAY161503, R-1065, YM348, and other compounds disclosed in U.S. Pat. No. 3,914,250, WO02/36596, WO02/48124, WO02/10169, WO01/66548, WO02/44152, WO02/51844, WO02/40456, WO02/40457 et al;
20) melanocortin-3 receptor agonists;
21) melanocortin-4 receptor agonists such as CHIR86036 (Chiron), ME-10142, ME-10145 (Melacure), and other compounds disclosed in WO99/64002, WO00/74679, WO01/991752, WO01/74844, WO01/70708, WO01/70337, WO01/91752, WO02/059095, WO02/059107, WO02/059108, WO02/059117, WO02/12166, WO02/11715, WO02/12178, WO02/15909, WO02/068387, WO02/068388, WO02/067869, WO03/007949, and WO03/009847 et al;
22) monoamine resorption inhibitors such as cibtramin (Meridia™/Reductil™) and its salts, and other compounds disclosed in U.S. Pat. No. 4,746,680, U.S. Pat. No. 4,806,570, U.S. Pat. No. 5,436,272, US Patent Application No. 2002/0006964, WO01/27068, and WO01/62341 et al;
23) serotonin re-uptake inhibitors such as dexfenfluramine, fluoxetine, and other compounds disclosed in U.S. Pat. No. 6,365,633, WO01/27060, and WO01/162341 et al;
24) glucagon-like peptide-1 agonists;
25) topiramate (Topimax™);
26) phytopharm compound 57 (e.g., CP644,673);
27) acetyl CoA carboxylase-2 (ACC2) inhibitors;
28) β-adrenalin receptor-3 agonists such as AD9677/TAK677 (Dai-Nippon Pharmaceutical/Takeda Chemical), CL-316,243, SB418790, BRL-37344, L-796568, BMS-196085, BRL-35135A, CGP12177A, BTA-243, W427353, trecadrine, Zeneca D7114, SR59119A, and other compounds disclosed in U.S. Pat. No. 5,705,515, U.S. Pat. No. 5,451,677, WO01/74782, and WO02/32897 et al;
29) diacylglycerol acyltransferase-1 inhibitors;
30) diacylglycerol acyltransferase-2 inhibitors,
31) fatty acid synthetase inhibitors such as carulenin, C75;
32) phosphodiesterase inhibitors such as theophylline, pentoxiphylline, zaprinast, sildenafil, amrinone, milrinone, cilostamide, rolipram, and cilomilast et al;
33) thyroid hormone-β agonists such as KB-2611 (KaroBio BMS), and other compounds disclosed in WO02/15845, JP-A-2000-256190 et al;
34) UCP (uncoupling protein)-1, 2, or 3 activators such as phytanic acid, 4-[(E)-2-(5,6,7,8-tetrahydro-5,5,8,8-tetramethyl-2-naphthalenyl-1-propenyl]benzoic acid (TT-NPB), retinoic acid, and other compounds disclosed in WO99/00123 et al;
35) acylestrogens such as oleoylestrone, and other compounds disclosed in del Mar-Grasa, M. et al., Obesity Research, 9:202-9 (2001);
36) glucocorticoid antagonists;
37) 11-β-hydroxysteroid dehydrogenase-1 inhibitors such as BVT3498, BVT2733, and other compounds disclosed in WO01/90091, WO01/90090, WO01/90092 et al;
38) stearoyl-CoA desaturase-1 inhibitors;
39) dipeptidyl peptidase-IV inhibitors such as isoleucine thiazolidine, valine pyrrolidide, NVP-DPP728, AF237, P93/01, TSL225, TMC-2A/2B/2C, FE999011, P9310/K364, VIP0177, SDZ274-444, and other compounds disclosed in WO03/004498, WO03/004496, EP1258476, WO02/083128, WO02/062764, WO03/000250, WO03/002530, WO03/002531, WO03/002553, WO03/002593, WO03/000180, and WO03/000181 et al;
40) lipase inhibitors such as tetrahydroliptatin (orlistat/Xenical™), Triton WR1339, RHC80267, lipstatin, tea saponin, diethylumbelliferyl phosphate, FL-386, WAY-121898, Bay-N-3176, valilactone, esteracin, ebelactone A, ebelactone B, RHC80267, and other compounds disclosed in WO01/77094, U.S. Pat. No. 4,598,089, U.S. Pat. No. 4,452,813, U.S. Pat. No. 5,512,565, U.S. Pat. No. 5,391,571, U.S. Pat. No. 5,602,151, U.S. Pat. No. 4,405,644, U.S. Pat. No. 4,189,438, and U.S. Pat. No. 4,242,453 et al;
41) fatty acid transporter inhibitors;
42) dicarboxylate transporter inhibitors;
43) glucose transporter inhibitors;
44) phosphate transporter inhibitors.

Those combination drugs are obtained by concurrent use of a compound of the invention with one, two or more of the above co-drugs. Furthermore, the combination drugs are useful for prevention or therapy of metabolic disorders, when combined with one, two or more drugs selected from the group consisting of diabetes-treating agents and hyperlipidemia-treating agents. Combinations containing, in particular, hypertension-treating agent and anti-obesity agent are useful for prevention or treatment for metabolic disorders with synergistic effect, when diabetes-treating agent and/or hyperlipidemia-treating agent are added thereto.

EXAMPLES

The invention is described more concretely with reference to the following Examples, to which, however, the invention should not be limited. As silica gel for columns, used was Wakogel™ C-200 (Wako Pure Chemical Industries); as a filled silica gel column, used was a FLASH+™ cartridge, KP-Sil or FPNH, FLASH12+M, FLASH25+S, FLASH25+M or FLASH40+M (Biotage Japan); as a pre-

Example 1

4-[(4-Fluorobenzyl)oxy]-1-(4-{(1E)-3-[isopropyl(methyl)amino]-1-propen-1-yl}phenyl)pyridin-2(1H)-one

(1) Production of 4-[(4-fluorobenzyl)oxy]-1-{4-[(1E)-3-hydroxy-1-propen-1-yl]phenyl}pyridin-2(1H)-one A mixture of 4-[(4-fluorobenzyl)oxy]pyridin-2(1H)-one (1.10 g, 5.0 mmol), (2E)-3-(4-bromophenyl)-2-propen-1-ol (1.28 g, 6 mmol), cuprous iodide (476 mg, 3 mmol), potassium carbonate (829 mg, 6 mmol) and DMF (20 mL) was stirred overnight at 155° C. The reaction liquid was cooled to room temperature, then poured into ammonia water, and ethyl acetate was added for extraction. The organic layer was washed with water and saturated saline, and dried with anhydrous magnesium sulfate. The solvent was concentrated under reduced pressure, followed by purification by flash column chromatography (KP-Sil, hexane:ethyl acetate=1:1 to 0:1) to obtain the entitled compound (881 mg).

(2) Production of 4-[(4-fluorobenzyl)oxy]-1-(4-{(1E)-3-[isopropyl(methyl)amino]-1-propen-1-yl}phenyl)pyridin-2(1H)-one Triethylamine (142 μL) and methanesulfonyl chloride (40 μL) were added at room temperature to a THF (3.0 mL) solution of the compound (120 mg) obtained in Example 1-(1). After stirred for 40 minutes, N-methylisopropylamine (500 μL) was added and stirred overnight. After concentrated, water and ethyl acetate were added. The organic layer was washed with saturated saline, dried with anhydrous magnesium sulfate, then concentrated to obtain the entitled compound (53 mg).

$^1$HNMR (400 MHz, CDCl$_3$, δ ppm): 1.06 (6H, d, J=6.5 Hz), 2.25 (3H, s), 2.90 (1H, septet, J=6.5 Hz), 3.21 (2H, d, J=6.8 Hz), 5.00 (2H, s), 6.01-6.05 (1H, m), 6.04 (1H, s), 6.27-6.35 (1H, m), 6.54 (2H, d, J=5.8 Hz), 7.10 (2H, dd, J=8.8 Hz, 8.4 Hz), 7.21-7.31 (3H, m), 7.40 (2H, dd, J=5.5, 8.4 Hz), 7.47 (2H, d, J=8.6 Hz);

Mass Spectrum (ESI): 407 (M+H).

Example 2

4-[(4-Fluorobenzyl)oxy]-1-{4-[(1E)-3-(isopropylamino)-1-propen-1-yl]phenyl}pyridin-2(1H)-one In the same manner as in Example 1-(2) but changing N-methylisopropylamine in Example 1-(2) to isopropylamine, the entitled compound was obtained.

$^1$HNMR (400 MHz, CDCl$_3$, δ ppm): 1.12 (6H, d, J=6.3 Hz), 2.91 (1H, septet, J=6.3 Hz), 3.44 (2H, d, J=6.1 Hz), 5.00 (2H, s), 6.01-6.05 (1H, m), 6.04 (1H, s), 6.33-6.39 (1H, m), 6.56 (2H, d, J=5.7 Hz), 7.10 (2H, dd, J=8.6, 8.6 Hz), 7.23 (1H, d, J=7.2 Hz), 7.29 (2H, d, J=8.4 Hz), 7.40 (2H, dd, J=5.3, 8.6 Hz), 7.46 (2H, d, J=8.6 Hz);

Mass Spectrum (ESI): 393 (M+H).

Example 3

4-[(4-Chlorobenzyl)oxy]-1-(4-{(1E)-3-[ethyl(methyl)amino]-1-propen-1-yl}phenyl)pyridin-2(1H)-one

(1) Production of 4-[(4-chlorobenzyl)oxy]-1-{4-[(1E)-3-hydroxy-1-propen-1-ylphenyl]pyridin-2(1H)-one In the same manner as in Example 1-(1) but changing 4-[(4-fluorobenzyl)oxy]pyridin-2(1H)-one to 4-[(4-chlorobenzyl)oxy]pyridin-2-(1H)-one in Example 1-(1), the entitled compound was obtained.

(2) Production of 4-[(4-chlorobenzyl)oxy]-1-(4-{(1E)-3-[ethyl(methyl)amino]-1-propen-1-yl}phenyl)pyridin-2(1H)-one In the same manner as in Example 1-(2) but changing, in Example 1-(2), the compound obtained in Example 1-(1) to the compound obtained in Example 3-(1) and changing N-methylisopropylamine to N-ethylmethylamine, the entitled compound was obtained.

$^1$HNMR (400 MHz, CDCl$_3$, δ ppm): 1.21 (3H, t, J=7.3 Hz), 2.39 (3H, s), 2.57-2.66 (2H, m), 3.33 (2H, d, J=5.4 Hz), 5.01 (2H, s), 6.02-6.06 (2H, m), 6.33-6.41 (1H, m), 6.60 (1H, d, J=15.6 Hz), 7.22-7.40 (7H, m), 7.50 (2H, d, J=8.8 Hz);

Mass Spectrum (ESI): 409 (M+H).

Examples 4 to 9

In the same manner as in Example 3-(2) but changing N-ethylmethylamine in Example 3-(2) to corresponding compounds, the compounds of Examples 4 to 9 were obtained.

Example 4

4-[(4-Chlorobenzyl)oxy]-1-(4-{(1E)-3-[propyl(methyl)amino]-1-propen-1-yl}phenyl)pyridin-2(1H)-one Using N-methylpropylamine, the entitled compound was synthesized.

$^1$HNMR (400 MHz, CDCl$_3$, δ ppm): 0.93 (3H, t, J=7.6 Hz), 1.60 (2H, q, J=7.5 Hz), 2.34 (3H, s), 2.44 (2H, d, J=7.3 Hz), 3.27 (2H, d, J=5.9 Hz), 5.01 (2H, s), 6.03-6.06 (2H, m), 6.35 (1H, dt, J=6.7, 15.9 Hz), 6.57 (1H, d, J=16.1 Hz), 7.22-7.40 (7H, m), 7.50 (2H, d, J=10.0 Hz);

Mass Spectrum (ESI): 423 (M+H).

Example 5

4-[(4-Chlorobenzyl)oxy]-1-(4-{(1E)-3-[isopropyl(methyl)amino]-1-propen-1-yl}phenyl)pyridin-2(1H)-one Using N-methylisopropylamine, the entitled compound was synthesized.

$^1$HNMR (400 MHz, CDCl$_3$, δ ppm): 1.13-1.26 (6H, m), 2.31 (3H, s), 3.04-3.05 (1H, m), 3.33 (2H, d, J=6.3 Hz), 5.01 (2H, s), 6.02-6.06 (2H, m), 6.35-6.42 (1H, m), 6.58 (1H, d, J=15.6 Hz), 7.22-7.40 (7H, m), 7.50 (2H, d, J=9.5 Hz);

Mass Spectrum (ESI): 423 (M+H).

Example 6

4-[(4-Chlorobenzyl)oxy]-1-(4-{(1E)-3-[butyl(methyl)amino]-1-propen-1-yl}phenyl)pyridin-2(1H)-one Using N-methylbutylamine, the entitled compound was synthesized.

$^1$HNMR (400 MHz, CDCl$_3$, δ ppm): 0.93 (3H, t, J=7.3 Hz), 1.29-1.40 (2H, m), 1.45-1.57 (2H, m), 2.28 (3H, s), 2.41 (2H, d, J=7.8 Hz), 3.19 (2H, d, J=6.3 Hz), 5.01 (2H, s), 6.02-6.06 (2H, m), 6.32 (1H, dt, J=6.7, 15.8 Hz), 6.54 (1H, d, J=15.6 Hz), 7.22-7.42 (7H, m), 7.50 (2H, d, J=9.3 Hz);

Mass Spectrum (ESI): 437 (M+H).

Example 7

4-[(4-Chlorobenzyl)oxy]-1-(4-{(1E)-3-[methyl(pyridin-2-ylmethyl)amino]-1-propen-1-yl}phenyl)pyridin-2(1H)-one Using methyl(pyridin-2-ylmethyl)amine, the entitled compound was synthesized.

$^1$HNMR (400 MHz, CDCl$_3$, δ ppm): 2.30 (3H, s), 3.27 (2H, d, J=6.3 Hz), 3.73 (2H, s), 5.02 (2H, s), 6.02-6.05 (2H, m), 6.36 (1H, dt, J=6.6, 15.9 Hz), 6.58 (1H, d, J=15.6 Hz), 7.13-7.54 (11H, m), 7.67 (1H, dt, J=1.8, 7.6 Hz), 8.57 (1H, dt, J=1.0, 4.9 Hz);

Mass Spectrum (ESI): 472 (M+H).

Example 8

4-[(4-Chlorobenzyl)oxy]-1-(4-[(1E)-3-(dimethylamino)-1-propen-1-yl]phenyl)pyridin-2(1H)-one Using dimethylamine (50%, aqueous solution), the entitled compound was synthesized.

$^1$HNMR (400 MHz, CDCl$_3$, δ ppm): 2.33 (6H, s), 3.16 (2H, d, J=6.3 Hz), 5.01 (2H, s), 6.02-6.05 (2H, m), 6.32 (1H, dt, J=6.7, 15.8 Hz), 6.57 (1H, d, J=15.6 Hz), 7.22-7.40 (7H, m), 7.49 (2H, dd, J=8.3, 16.6 Hz);

Mass Spectrum (ESI): 395 (M+H).

Example 9

4-[(4-Chlorobenzyl)oxy]-1-(4-[(1E)-3-(methylamino)-1-propen-1-yl]phenyl)pyridin-2(1H)-one Using methylamine (40%, methanol solution), the entitled compound was synthesized.

$^1$HNMR (400 MHz, CDCl$_3$, δ ppm): 2.55 (3H, s), 3.54 (2H, d, J=6.3 Hz), 5.02 (2H, s), 6.02-6.05 (2H, m), 6.30-6.38 (1H, m), 6.58 (1H, d, J=15.6 Hz), 7.22-7.40 (7H, m), 7.49 (2H, dd, J=5.9, 15.3 Hz);

Mass Spectrum (ESI): 381 (M+H).

Example 10

4-[(E)-2-(4-fluorophenyl)vinyl]-1-(4-{(1E)-3-[isopropyl(methyl)amino]-1-propen-1-yl}phenyl)pyridin-2(1H)-one (1) Production of 4-iodo-2-(4-methoxybenzyloxy)pyridine With cooling with ice, sodium hydride (60% oily, 4.93 g, 0.188 mmol) was added to a DMF (250 mL) solution of 4-methoxybenzyl alcohol (17.04 g), and stirred for 30 minutes. 2-Fluoro-4-iodopyridine (25.0 g) was added, and stirred at room temperature for 2 hours. Water was added to the reaction liquid, and extracted with diethyl ether. The organic layer was washed with saturated saline, and dried with anhydrous magnesium sulfate. The solvent was concentrated under reduced pressure, then diisopropyl ether was added to the obtained residue, and the obtained solid was collected by filtration to obtain the entitled compound (26.15 g, 68%).

(2) Production of 4-[(E)-2-(4-fluorophenyl)vinyl]-2-(4-methoxybenzyloxy)pyridine 4-Fluorostyrene (3.0 mL), dichlorobis(triphenylphosphine)palladium (870 mg) and potassium carbonate (5.2 g) were added to a DMF (70 mL) solution of the compound obtained in (1) (4.25 g), and stirred at 100° C. for 19 hours. Saturated saline was added to the reaction liquid, extracted with ethyl acetate, and dried with anhydrous magnesium sulfate. The solvent was concentrated under reduced pressure, and the obtained residue was purified by silica gel column chromatography (C-200, ethyl acetate:hexane=1:19 to 1:9 to 1:4) to obtain the entitled compound (2.55 g, 61%).

(3) Production of 4-[(E)-2-(4-fluorophenyl)vinyl]pyridin-2(1H)-one

Trifluoroacetic acid (15 mL) was added to a chloroform (15 mL) solution of the compound obtained in (2) (2.5 g), and stirred at room temperature for 1 hour. The reaction liquid was concentrated under reduced pressure, diethyl ether was added to the obtained residue, and the obtained solid was collected by filtration to obtain the entitled compound (1.63 g, 100%).

(4) Production of 4-[(E)-2-(4-fluorophenyl)vinyl]-1-(4-{(1E)-3-[isopropyl(methyl)amino]-1-propen-1-yl}phenyl)pyridin-2(1H)-one In the same manner as in Example 1 but using the compound obtained in Example 10-(3) in place of 4-[(4-fluorobenzyl)oxy]pyridin-2(1H)-one in Example 1-(1), the entitled compound was obtained.

$^1$HNMR (400 MHz, CDCl$_3$, δ ppm): 1.25-1.27 (6H, m), 2.44-2.47 (3H, brs), 3.49-3.51 (2H, m), 6.48-6.51 (2H, m), 6.63-6.68 (2H, m), 6.84 (1H, d, J=16.2 Hz), 7.07 (2H, dd, J=8.4, 8.8 Hz), 7.17 (1H, d, J=16.2 Hz), 7.32 (1H, d, J=7.2), 7.38 (2H, d, J=8.4 Hz), 7.50-7.55 (4H, m);

Mass Spectrum (ESI): 403 (M+H).

Example 11

4-[(E)-2-(phenyl)vinyl]-1-(4-{(1E)-3-[isopropyl(methyl)amino]-1-propen-1-yl}phenyl)pyridin-2(1H)-one (1) Production of 1-{4-[(E)-3-hydroxy-1-propen-1-yl]phenyl}-4-methylpyridin-2(1H)-one In the same manner as in Example 1-(1) but changing 4-[(4-fluorobenzyl)oxy]pyridin-2(1H)-one to 2-hydroxy-4-methylpyridine in Example 1-(1), the entitled compound was obtained.

(2) Production of 1-{4-[(E)-3-hydroxy-1-propen-1-yl]phenyl}-4-[(E)-2-phenylvinyl]pyridin-2(1H)-one Sodium hydride (50 to 72%, 96 mg) was added to a DMF (3 mL) solution of the compound obtained in (1) (241 mg, 1.0 mmol) and benzaldehyde (303 μL, 3.0 mmol), and stirred overnight. Water was added to the reaction liquid, and extracted with ethyl acetate. The organic layer was washed with water and saturated saline, and dried with anhydrous magnesium sulfate. The solvent was concentrated under reduced pressure, and purified by flash column chromatography (KP-Sil, hexane:ethyl acetate=1:1 to 1:4) to obtain the entitled compound (77.8 mg).

(3) Production of 4-[(E)-2-(phenyl)vinyl]-1-(4-{(1E)-3-[isopropyl(methyl)amino]-1-propen-1-yl}phenyl)pyridin-2(1H)-one In the same manner as in Example 1-(2) but changing, in Example 1-(2), the compound obtained in Example 1-(1) to the compound obtained in Example 11-(2), the entitled compound was obtained.

$^1$HNMR (400 MHz, CDCl$_3$, δ ppm): 1.22-1.25 (6H, m), 2.40-2.44 (3H, brs), 3.49-3.51 (2H, m), 6.50-6.52 (2H, m), 6.61-6.65 (2H, m), 6.93 (1H, d, J=16.4 Hz), 7.21 (1H, d, J=16.4 Hz), 7.31-7.42 (6H, m), 7.51-7.56 (4H, m);

Mass Spectrum (ESI): 385(M+H)

Example 12

4-[(E)-2-phenylvinyl]-1-(4-{(1E)-3-[ethyl(methyl)amino]-1-propen-1-yl}phenyl)pyridin-2(1H)-one In the same manner as in Example 11-(3) but changing N-methylisopropylamine to N-ethylmethylamine in Example 11-(3), the entitled compound was obtained.

$^1$HNMR (400 MHz, CDCl$_3$, δ ppm): 1.16 (3H, t, J=7.0 Hz), 2.33 (3H, s), 2.56 (2H, q, J=7.0 Hz), 3.26 (2H, d, J=6.9 Hz), 6.32-6.40 (1H, m), 6.51 (1H, dd, J=2.0, 7.1 Hz), 6.93 (1H, d, J=16.4 Hz), 7.21 (1H, d, J=16.4 Hz), 7.30-7.42 (6H, m), 7.48-7.56 (4H, m);

Mass Spectrum (ESI): 371 (M+H)

Example 13

1-[4-(1-Ethylpiperidin-4-yl)phenyl]-4-F(4-fluorobenzyl)oxy]pyridin-2(1H)-one (1) Production of 1-ethyl-4-(4-iodophenyl)piperidine A dichloromethane (36 mL) mixture of 1-ethyl-4-phenylpiperidine (1.37 g, 7.23 mmol), acetic acid (500 μL), silver trifluoromethanesulfonate (3.72 g), and iodine (3.67 g) was stirred overnight. Ethyl acetate was added, then the insoluble matter was removed by filtration. The obtained filtrate was washed with ammonia water, aqueous sodium thiosulfate solution and saturated saline. After dried with anhydrous magnesium sulfate, this was concentrated and purified by flash column chromatography (FPNH, hexane:ethyl acetate=1 to 9:1) to obtain a mixture of the entitled compound and 1-ethyl-4-phenylpiperidine (2.52 g).

(2) Production of 1-[4-(1-ethylpiperidin-4-yl)phenyl]-4-[(4-fluorobenzyl)oxy]pyridin-2(1H)-one In the same manner as in Example 1-(1), but changing, in Example 1-(1), (2E)-3-(4-bromophenyl)-2-propen-1-ol to the compound obtained in Example 13-(1), the entitled compound was obtained.

$^1$HNMR (400 MHz, CDCl$_3$, δ ppm): 1.13 (3H, t, J=7.2 Hz), 1.79-1.86 (4H, m), 1.98-2.04 (2H, m), 2.46 (2H, q, J=7.2 Hz), 2.52-2.57 (1H, m), 3.09 (2H, d, J=11.7 Hz), 4.99 (2H, s), 6.00-6.06 (2H, m), 7.10 (2H, dd, J=8.6, 8.7 Hz), 7.23 (1H, d, J=7.6 Hz), 7.27-7.34 (4H, m), 7.40 (2H, dd, J=5.3, 8.8 Hz);

Mass Spectrum (ESI): 407 (M+H)

Example 14

4-[(4-Fluorobenzyl)oxy]-1-{4-[(2-pyrrolidin-1-yl-ethyl)amino]phenyl}pyridin-2(1H)-one (1) Production of Methyl 4-[4-[(4-fluorobenzyl)oxy]-2-oxopyridin-1(2)-yl]benzoate A mixture of 4-[(4-fluorobenzyl)oxy]pyridin-2(1H)-one (1.57 g, 7.16 mmol), [4-(methoxycarbonyl)phenyl]boric acid (3.86 g, 21.4 mmol), cupric acetate (2.0 g, 11.0 mmol), pyridine (1.2 mL, 14.8 mmol), molecular sieve 4A (2.0 g) and chloroform (100 mL) was stirred at room temperature for 2 days. Chloroform and water were added to the reaction liquid, the insoluble matter was separated by filtration, the organic layer was washed with 5% ammonia water and saturated saline, and dried with anhydrous magnesium sulfate. The solvent was concentrated under reduced pressure, and the obtained residue was purified by silica gel column chromatography (C-300, methanol:chloroform=1:100 to 3:97) to obtain the entitled compound (1.34 mg, 47%).

(2) Production of 4-[4-[(4-fluorobenzyl)oxy]-2-oxopyridin-1(2)-yl]benzoic Acid

Aqueous 4 N sodium hydroxide solution (20 mL) was added to a methanol (100 mL)/THF (100 mL) solution of the compound obtained in (1) (1.34 g, 3.79 mmol), and stirred at room temperature for 3 hours. The reaction liquid was made acidic with 1 N hydrochloric acid, then extracted with ethyl acetate, and dried with anhydrous magnesium sulfate. The reaction liquid was concentrated under reduced pressure to obtain the entitled compound (1.29 g, 100%).

(3) Production of Tert-Butyl {4-[4-[(4-fluorobenzyl)oxy]-2-oxopyridin-[(2)-yl]phenyl}carbamate A mixture of the compound obtained in (2) (340 mg, 1.00 mmol), diphenylphosphorylazide (430 μL, 2.00 mmol), tert-butanol (190 μL, 2.03 mmol), triethylamine (280 μL, 2.03 mmol) and N,N-dimethylformamide (5 mL) was stirred at 100° C. for 4.5 hours. The reaction liquid was left cooled, then saturated saline was added, extracted with chloroform and dried with anhydrous magnesium sulfate. The solvent was concentrated under reduced pressure, and the obtained residue was purified by silica gel column chromatography (C-200, methanol:chloroform=1:99 to 3:97) to obtain the entitled compound (53 mg, 13%).

(4) Production of Tert-Butyl {4-[4-[(4-fluorobenzyl)oxy]-2-oxopyridin-1(2)-yl]phenyl}(2-pyrrolidin-1-ylethyl)carbamate Potassium tert-butoxide (41 mg, 0.366 mmol) was added to a THF solution of the compound obtained in (3) (50 mg, 0.122 mmol), and stirred at room temperature for 1 hour. 1-(2-Chloroethyl)pyrrolidine hydrochloride (41 mg, 0.241 mmol) was added to the reaction liquid, then stirred overnight at 70° C. The reaction liquid was left cooled, then saturated saline was added, extracted with chloroform, and dried with anhydrous magnesium sulfate. The solvent was concentrated under reduced pressure, and the obtained residue was purified by preparative thin-layer chromatography (methanol:chloroform=1:10) to obtain the entitled compound (62 mg, 100%).

(5) Production of 4-[(4-fluorobenzyl)oxy]-1-{4-[(2-pyrrolidin-1-ylethyl)amino]phenyl}pyridin-2(1H)-one Trifluoroacetic acid (2 mL) was added to a chloroform solution of the compound obtained in (4) (62 mg, 0.122 mmol), and stirred at room temperature for 1 hour. The reaction liquid was concentrated under reduced pressure, aqueous 1 N sodium hydroxide solution was added, extracted with chloroform, and dried with anhydrous magnesium sulfate. The solvent was concentrated under reduced pressure, and the obtained residue was purified by preparative thin-layer chromatography (methanol:chloroform=1:4) to obtain the entitled compound (11 mg, 22%).

$^1$HNMR (400 MHz, CDCl$_3$, δ ppm): 1.80-1.89 (4H, m), 2.60-2.69 (4H, m), 2.82 (2H, t, J=5.9 Hz), 3.22-3.29 (2H, m), 4.62-4.73 (1H, m), 4.98 (2H, s), 5.98 (1H, dd, J=2.4, 7.3 Hz), 6.03 (1H, d, J=2.4 Hz), 6.67 (2H, d, J=8.8 Hz), 7.10 (2H, d, J=8.8 Hz), 7.12 (2H, d, J=8.8 Hz), 7.22 (1H, d, J=7.3 Hz), 7.39 (2H, dd, J=5.4, 8.8 Hz);

Mass Spectrum (ESI): 407 (M+H)

Example 15

4-(Benzyloxy)-1-(4-{[2-(diethylamino)ethyl]amino}phenyl)pyridin-2(1H)-one

In the same manner as in Example 14 but changing 4-[(4-fluorobenzyl)oxy]pyridin-2(1H)-one to (4-benzyloxy)pyridin-2(1H)-one in Example 14-(1), and changing 1-(2-chloroethyl)pyrrolidine hydrochloride to (2-bromoethyl)diethylamine hydrobromide in Example 14-(4), the entitled compound was obtained.

$^1$HNMR (400 MHz, CDCl$_3$, δ ppm): 1.03 (6H, t, J=7.1 Hz), 2.57 (4H, q, J=7.1 Hz), 2.71 (2H, t, J=5.9 Hz), 3.08-3.19 (2H, m), 4.50-4.67 (1H, m), 5.03 (2H, s), 6.00 (1H, dd, J=2.6, 7.6 Hz), 6.06 (1H, d, J=2.6 Hz), 6.66 (2H, d, J=8.7 Hz), 7.13 (2H, d, J=8.7 Hz), 7.22 (1H, d, J=7.6 Hz), 7.30-7.48 (5H, m);

Mass Spectrum (ESI): 392 (M+H)

Example 16

1-{4-[[2-(Diethylamino)ethyl](methyl)amino]phenyl}-4-(benzyloxy)-pyridin-2(1H)-one Aqueous 37% formalin solution (100 μL) and 0.3 mol Zn[B(CN)H$_3$]$_2$/methanol solution (1.0 mL, 0.3 mmol, prepared from ZnCl$_2$ and NaB(CN)H$_3$) were added to a methanol solution (1 mL) of the compound obtained in Example 15 (7 mg, 0.018 mmol), and stirred at room temperature for 45 minutes. Aqueous 1 N sodium hydroxide solution was added to the reaction liquid, extracted with chloroform, dried with anhydrous magnesium sulfate. The solvent was concentrated under reduced pressure to obtain the entitled compound (2.8 mg, 39%).

$^1$HNMR (400 MHz, CDCl$_3$, δ ppm): 1.06 (6H, t, J=7.1 Hz), 2.52-2.72 (2H, m), 2.61 (4H, q, J=7.1 Hz), 3.42-3.52 (2H, m), 2.99 (3H, s), 5.03 (2H, s), 6.00 (1H, dd, J=2.7, 7.6 Hz), 6.06 (1H, d, J=2.7 Hz), 6.72 (2H, d, J=9.0 Hz), 7.17 (2H, d, J=9.0 Hz), 7.22 (1H, d, J=7.6 Hz), 7.32-7.45 (5H, m);

Mass Spectrum (ESI): 392 (M+H)

Example 17

4-[(4-Fluorobenzyl)oxy]-1-[4-(3-pyrrolidin-1-ylpropyl)phenyl]pyridin-2(1H)-one

(1) Production of 2-[3-(4-iodophenyl)propoxy]tetrahydro-2H-pyran 3,4-Dihydro-2H-pyran (2.5 mL, 27.4 mmol) and pyridinium p-toluenesulfonate (450 mg, 1.79 mmol) were added to a chloroform (50 mL) solution of 3-(4-iodophenyl)propan-1-ol (4.73 g, 18.0 mmol), and stirred overnight at room temperature. The reaction liquid was diluted with chloroform, washed with saturated saline, dried with anhydrous magnesium sulfate. The solvent was concentrated under reduced pressure, and the obtained residue was purified by silica gel column chromatography (C-200, ethyl acetate:hexane=1:9 to 1:4) to obtain the entitled compound (6.22 g, 100%).

(2) Production of 4-[(4-fluorobenzyl)oxy]-1-{4-[3-(tetrahydro-2H-pyran-2-yloxy)propyl]phenyl}pyridin-2(1H)-one In the same manner as in Example 1-(1) but changing (2E)-3-(4-bromophenyl)-2-propen-1-ol in Example 1-(1) to the compound obtained in Example 17-(1), the entitled compound was obtained.

(3) Production of 4-[(4-fluorobenzyl)oxy]-1-[4-(3-hydroxypropyl)phenyl]pyridin-2(1H)-one 1 N hydrochloric acid (5 mL) was added to a methanol (5 mL)-THF (5 mL) solution of the compound obtained in (2) (313 mg, 0.715 mmol), and stirred at room temperature for 55 minutes. Saturated saline was added to the reaction liquid, extracted with ethyl acetate and dried with anhydrous magnesium sulfate. The solvent was concentrated under reduced pressure, and the obtained residue was purified by silica gel column chromatography (C-200, methanol:chloroform=3:97 to 1:19) to obtain the entitled compound (150 mg, 23%).

(4) Production of 4-[(4-fluorobenzyl)oxy]-1-[4-(3-pyrrolidin-1-ylpropyl)phenyl]pyridin-2(1H)-one In the same manner as in Example 1-(2) but changing, in Example 1-(2), the compound obtained in Example 1-(1) to the compound obtained in Example 17-(3) and changing N-methylisopropylamine to pyrrolidine, the entitled compound was obtained.

$^1$HNMR (400 MHz, CDCl$_3$, δ ppm): 1.70-1.85 (4H, m), 1.88 (2H, quint, J=7.9 Hz), 2.42-2.60 (4H, m), 2.51 (2H, t, J=7.9H), 2.70 (2H, t, J=7.9 Hz), 5.00 (2H, s), 5.98-6.08 (2H, m), 7.10 (2H, t, J=8.8 Hz), 7.19-7.34 (5H, m), 7.40 (2H, dd, J=5.3, 8.8 Hz);

Mass Spectrum (ESI): 407 (M+H)

Example 18

1-{4-[3-(Diethylamino)propyl]phenyl}-4-[(4-fluorobenzyl)oxy]pyridin-2(1H)-one In the same manner as in Example 17-(3) but changing pyrrolidine in Example 17-(3) to diethylamine, the entitled compound was obtained.

$^1$HNMR (400 MHz, CDCl$_3$, δ ppm): 1.38 (6H, t, J=7.3 Hz), 2.17-2.32 (2H, m), 2.80 (2H, t, J=7.4 Hz), 2.92-3.03 (2H, m), 3.03-3.20 (4H, m), 5.00 (2H, s), 6.01-6.08 (2H, m), 7.10 (2H, t, J=8.6 Hz), 7.20-7.25 (1H, m), 7.31 (4H, s), 7.40 (2H, dd, J=5.4, 8.6 Hz);
Mass Spectrum (ESI): 409 (M+H)

Example 19

4-[(5-Chloropyridin-2-yl)methoxy]-1-[4-(3-pyrrolidin-1-ylpropyl)phenyl]pyridin-2(1H)-one

(1) Production of 4-hydroxy-1-{4-[3-(tetrahydro-2H-pyran-2-yloxy)propyl]phenyl}pyridin-2(1H)-one 10% palladium-carbon (200 mg) was added to a THF (20 mL)-methanol (20 mL) solution of the compound obtained in Example 17-(1) (630 mg, 1.44 mmol), and stirred in a hydrogen atmosphere at room temperature for 4 hours. The reaction liquid was filtered, well washed with methanol, then the filtrate was concentrated under reduced pressure, and the obtained residue was purified by silica gel column chromatography (C-200, methanol:chloroform=3:97 to 1:19) to obtain the entitled compound (395 mg, 83%).

(2) Production of 4-[(5-chloropyridin-2-yl)methoxy]-1-{4-[3-(tetrahydro-2H-pyran-2-yloxy)propyl]phenyl}pyridin-2(1H)-one The compound obtained in (1) (390 mg, 1.18 mmol), (5-chloropyridin-2-yl)methanol (340 mg, 2.37 mmol), tri-n-butyl phosphine (0.90 mL, 3.61 mmol) and 1,1'-(azodicarbonyl)dipiperidine (900 mg, 3.61 mmol) were stirred overnight in THF (20 mL) at room temperature. Saturated saline was added to the reaction liquid, extracted with ethyl acetate, and dried with anhydrous magnesium sulfate. The solvent was concentrated under reduced pressure, n-hexane was added to the obtained residue, and the insoluble matter was collected by filtration and purified by silica gel column chromatography (C-200, ethyl acetate) to obtain the entitled compound (263 mg, 49%).

(3) Production of 4-[(5-chloropyridin-2-yl)methoxy]-1-[4-(3-hydroxypropyl)phenyl]pyridin-2(1H)-one In the same manner as in Example 17-(4) but changing, in Example 17-(4), the compound obtained in Example 17-(3) to the compound obtained in Example 19-(2), the entitled compound was obtained.

(4) Production of 4-[(5-chloropyridin-2-yl)methoxy]-1-[4-(3-pyrrolidin-1-ylpropyl)phenyl]pyridin-2(1H)-one In the same manner as in Example 17-(4) but changing, in Example 17-(4), the compound obtained in Example 17-(3) to the compound obtained in Example 19-(3), the entitled compound was obtained.

$^1$HNMR (400 MHz, CDCl$_3$, δ ppm): 1.42-1.80 (4H, m), 2.00-2.36 (6H, m), 2.80 (2H, t, J=7.2 Hz), 2.97-3.04 (2H, m), 5.16 (2H, s), 6.02 (1H, d, J=2.8 Hz), 6.11 (1H, dd, J=2.8, 7.6 Hz), 7.20-7.34 (5H, m), 7.44 (1H, d, J=8.4 Hz), 7.74 (1H, dd, J=2.4, 8.4 Hz), 8.58 (1H, d, J=2.4 Hz);
Mass Spectrum (ESI): 424 (M+H)

Example 20

4-[(5-Chloropyridin-2-yl)methoxy]-1-{4-[3-(diethylamino)propyl]phenyl}pyridin-2(1H)-one In the same manner as in Example 19-(4) but changing pyrrolidine in Example 19-(4) to diethylamine, the entitled compound was obtained.

$^1$HNMR (400 MHz, CDCl$_3$, δ ppm): 1.38 (6H, t, J=7.3 Hz), 2.15-2.29 (2H, m), 2.79 (2H, t, J=7.3 Hz), 2.92-3.03 (2H, m), 3.10 (4H, q, J=7.3 Hz), 5.16 (2H, s), 6.02 (1H, d, J=2.7 Hz), 6.11 (1H, dd, J=2.7, 7.7 Hz), 7.20-7.30 (1H, m), 7.31 (4H, s), 7.44 (1H, d, J=8.3 Hz), 7.73 (1H, dd, J=2.5, 8.3 Hz), 8.58 (1H, d, J=2.5 Hz);
Mass Spectrum (ESI): 426 (M+H)

Example 21

4-[(4-Fluorobenzyl)oxy]-1-[4-(2-pyrrolidin-1-ylethyl)phenyl]pyridin-2(1H)-one

(1) Production of 4-[(4-fluorobenzyl)oxy]-1-{4-[2-(tetrahydro-2H-pyran-2-yloxy)ethyl]phenyl}pyridin-2(1H)-one In the same manner as in Example 1-(1) but changing (2E)-3-(4-bromophenyl)-2-propen-1-ol in Example 1-(1) to 2-[2-(4-iodophenyl)ethoxy]tetrahydro-2H-pyran, the entitled compound was obtained.

(2) Production of 4-[(4-fluorobenzyl)oxy]-1-[4-(2-hydroxyethyl)phenyl]pyridin-2(1H)-one In the same manner as in Example 17-(4) but changing, in Example 17-(4), the compound obtained in Example 17-(3) to the compound obtained in Example 21-(1), the entitled compound was obtained.

(3) Production of 2-{4-[4-[(4-fluorobenzyl)oxy]-2-oxopyridin-1(2H)-yl]phenyl}ethyl methanesulfonate Triethylamine (1.5 mL, 10.8 mmol) was added to a chloroform (70 mL)-THF (140 mL) solution of the compound obtained in (2) (1.83 g, 5.39 mmol), then methanesulfonyl chloride (0.63 mL, 8.14 mmol) was added and stirred at room temperature for 2 hours. Saturated sodium bicarbonate water was added to the reaction liquid, extracted with chloroform, and dried with anhydrous magnesium sulfate. The solvent was concentrated under reduced pressure to obtain the entitled compound (2.25 g, 100%).

(4) Production of 1-[4-(2-bromoethyl)phenyl]-4-[(4-fluorobenzyl)oxy]pyridin-2(1H)-one Sodium bromide (6.0 g, 58.3 mmol) was added to a DMF (40 mL) solution of the compound obtained in (3) (2.25 g, 5.39 mmol), and stirred overnight at 50° C. Water was added to the reaction liquid, extracted with ethyl acetate, and dried with anhydrous magnesium sulfate. The solvent was concentrated under reduced pressure, and the obtained residue was purified by silica gel column chromatography (C-200, methanol:chloroform=1:99 to 3:97) to obtain the entitled compound (2.03 mg, 94%).

(5) Production of 4-[(4-fluorobenzyl)oxy]-1-[4-(2-pyrrolidin-1-ylethyl)phenyl]pyridin-2(1H)-one Pyrrolidine (0.1 mL, 1.20 mmol) and potassium carbonate (33 mg, 0.239 mmol) were added to a DMF (3 mL) solution of the compound obtained in (4) (48 mg, 0.119 mmol), and stirred overnight at 50° C. Aqueous 1 N sodium hydroxide solution was added to the reaction liquid, extracted with chloroform, and dried with anhydrous magnesium sulfate. The solvent was concentrated under reduced pressure, and the obtained residue was purified by silica gel column chromatography (C-200, methanol:chloroform:ammonia water=1: 19:0 to 1:4:0 to 1:4:1) to obtain the entitled compound (31 mg, 66%).

$^1$HNMR (400 MHz, CDCl$_3$, δ ppm): 1.75-1.95 (4H, m), 2.58-3.02 (8H, m), 5.00 (2H, s), 6.03 (1H, d, J=6.8 Hz), 6.04 (1H, s), 7.10 (2H, t, J=8.6 Hz), 7.22 (1H, d, J=6.8 Hz), 7.27 (2H, d, J=8.3 Hz), 7.33 (2H, d, J=8.3 Hz), 7.40 (2H, dd, J=5.3, 8.6 Hz);

Mass Spectrum (ESI): 393 (M+H)

Examples 22 to 30

In the same manner as in Example 21-(5) but changing pyrrolidine in Example 21-(5) to corresponding compounds, the compounds of Examples 22 to 30 were obtained.

Example 22

4-[(4-Fluorobenzyl)oxy]-1-(4-{2-[(2-methoxyethyl) (methyl)amino]ethyl}phenyl)pyridin-2(1H)-one Using (2-methoxyethyl)methylamine, the entitled compound was synthesized.

$^1$HNMR (400 MHz, CDCl$_3$, δ ppm): 2.38 (3H, s), 2.58-2.95 (6H, m), 3.37 (3H, s), 3.45-3.60 (2H, m), 5.00 (2H, s), 6.02 (1H, dd, J=2.9, 7.3 Hz), 6.04 (1H, d, J=2.9 Hz), 7.10 (2H, t, J=8.8 Hz), 7.22 (1H, d, J=7.3 Hz), 7.26 (2H, d, J=8.3 Hz), 7.30 (2H, d, J=8.3 Hz), 7.40 (2H, dd, J=5.4, 8.8 Hz);

Mass Spectrum (ESI): 411 (M+H)

Example 23

1-{4-[2-(cyclopentylamino)ethyl]phenyl}-4-[(4-fluorobenzyl)oxy]pyridin-2(1H)-one Using cyclopentylamine, the entitled compound was synthesized.

$^1$HNMR (400 MHz, CDCl$_3$, δ ppm): 1.30-2.00 (8H, m), 2.91 (4H, s), 3.12 (1H, quint, J=7.0 Hz), 5.00 (2H, s), 6.04 (1H, d, J=7.3 Hz), 6.04 (1H, s), 7.10 (2H, t, J=8.5 Hz), 7.22 (1H, d, J=7.3 Hz), 7.28 (2H, d, J=8.3 Hz), 7.33 (2H, d, J=8.3 Hz), 7.40 (2H, dd, J=5.1, 8.5 Hz);

Mass Spectrum (ESI): 407 (M+H)

Example 24

4-[(4-Fluorobenzyl)oxy]-1-{4-[2-(isopropylamino) ethyl]phenyl}pyridin-2(1H)-one

Using isopropylamine, the entitled compound was synthesized.

$^1$HNMR (400 MHz, CDCl$_3$, δ ppm): 1.12 (6H, d,=6.3 Hz), 2.85-2.96 (1H, m), 2.92 (4H, s), 5.00 (2H, s), 6.03 (1H, d, J=7.3 Hz), 6.04 (1H, s), 7.10 (2H, t, J=8.5 Hz), 7.22 (1H, d, J=7.3 Hz), 7.28 (2H, d, J=8.8 Hz), 7.33 (2H, d, J=8.8 Hz), 7.40 (2H, dd, J=5.1, 8.5 Hz);

Mass Spectrum (ESI): 381 (M+H)

Example 25

4-[(4-Fluorobenzyl)oxy]-1-(4-{2-[(2-methoxyethyl) amino]ethyl}phenyl)pyridin-2(1H)-one Using methoxyethylamine, the entitled compound was synthesized.

$^1$HNMR (400 MHz, CDCl$_3$, δ ppm): 2.82-2.98 (6H, m), 3.36 (3H, s), 3.52 (2H, t, J=5.4 Hz), 5.00 (2H, s), 6.03 (1H, dd, J=2.4, 7.3 Hz), 6.05 (1H, d, J=2.4 Hz), 7.10 (2H, t, J=8.8 Hz), 7.22 (1H, d, J=7.3 Hz), 7.27 (2H, d, J=8.3 Hz), 7.32 (2H, d, J=8.3 Hz), 7.40 (2H, dd, J=5.4, 8.8 Hz);

Mass Spectrum (ESI): 397 (M+H)

Example 26

4-[(4-Fluorobenzyl)oxy]-1-(4-{2-[(3R)-3-methoxypyrrolidin-1-yl]ethyl}phenyl)pyridin-2(1H)-one Using (3R)-3-methoxypyrrolidine, the entitled compound was synthesized.

$^1$HNMR (400 MHz, CDCl$_3$, δ ppm): 1.80-1.95 (1H, m), 2.03-2.19 (1H, m), 2.40-3.04 (8H, m), 3.31 (3H, s), 3.91-4.01 (1H, m), 5.00 (2H, s), 6.02 (1H, dd, J=2.4, 7.3 Hz), 6.04 (1H, d, J=2.4 Hz), 7.10 (2H, t, J=8.3 Hz), 7.22 (1H, d, J=7.3 Hz), 7.26 (2H, d, J=8.3 Hz), 7.31 (2H, d, J=8.3 Hz), 7.40 (2H, dd, J=5.4, 8.3 Hz);

Mass Spectrum (ESI): 423 (M+H)

Example 27

4-[(4-Fluorobenzyl)oxy]-1-(4-{2-[(3S)-3-methoxypyrrolidin-1-yl]ethyl}phenyl)pyridin-2(1H)-one Using (3S)-3-methoxypyrrolidine, the entitled compound was synthesized.

$^1$HNMR (400 MHz, CDCl$_3$, δ ppm): 1.80-1.95 (1H, m), 2.03-2.19 (1H, m), 2.40-3.04 (8H, m), 3.31 (3H, s), 3.91-4.01 (1H, m), 5.00 (2H, s), 6.03 (1H, dd, J=2.4, 7.3 Hz), 6.04 (1H, d, J=2.4 Hz), 7.06 (2H, t, J=8.3 Hz), 7.22 (1H, d, J=7.3 Hz), 7.26 (2H, d, J=8.3 Hz), 7.31 (2H, d, J=8.3 Hz), 7.40 (2H, dd, J=5.9, 8.3 Hz);

Mass Spectrum (ESI): 423 (M+H)

Example 28

4-[(4-Fluorobenzyl)oxy]-1-(4-{2-[(2S)-2-(methoxymethyl)pyrrolidin-1-yl]ethyl}phenyl)pyridin-2 (1H)-one Using (2S)-2-(methoxymethyl)pyrrolidine, the entitled compound was synthesized.

$^1$HNMR (400 MHz, CDCl$_3$, δ ppm): 1.40-3.52 (13H, m), 3.35 (3H, s), 5.00 (2H, s), 6.03 (1H, dd, J=2.4, 7.3 Hz), 6.05 (1H, d, J=2.4 Hz), 7.10 (2H, t, J=8.8 Hz), 7.22 (1H, d, J=7.3 Hz), 7.26 (2H, d, J=8.8 Hz), 7.32 (2H, d, J=8.8 Hz), 7.40 (2H, dd, J=5.4, 8.8 Hz);

Mass Spectrum (ESI): 437 (M+H)

Example 29

4-[(4-Fluorobenzyl)oxy]-1-(4-{2-[(3R)-3-fluoropyrolidin-1-yl]ethyl}phenyl)pyridin-2(1H)-one

Using (3R)-3-fluoropyrrolidine, the entitled compound was synthesized.
$^1$HNMR (400 MHz, CDCl$_3$, δ ppm): 1.93-3.08 (10H, m), 5.00 (2H, s), 5.07-5.33 (1H, m), 6.03 (1H, dd, J=7.3, 2.4 Hz), 6.04 (1H, d, J=2.4 Hz), 7.10 (2H, t, J=8.8 Hz), 7.22 (1H, d, J=7.3 Hz), 7.27 (2H, d, J=8.8 Hz), 7.32 (2H, d, J=8.8 Hz), 7.40 (2H, dd, J=8.8, 5.4 Hz);
Mass Spectrum (ESI): 411 (M+H)

Example 30

4-[(4-Fluorobenzyl)oxy]-1-(4-{2-[(3S)-3-fluoropyrolidin-1-yl]ethyl}phenyl)pyridin-2(1H)-one

Using (3S)-3-fluoropyrrolidine, the entitled compound was synthesized.
$^1$HNMR (400 MHz, CDCl$_3$, δ ppm): 1.93-3.08 (10H, m), 5.00 (2H, s), 5.07-5.33 (1H, m), 6.03 (1H, dd, J=2.4, 7.3 Hz), 6.04 (1H, d, J=2.4 Hz), 7.10 (2H, t, J=8.8 Hz), 7.22 (1H, d, J=7.3 Hz), 7.27 (2H, d, J=8.8 Hz), 7.32 (2H, d, J=8.8 Hz), 7.40 (2H, dd, J=5.4, 8.8 Hz);
Mass Spectrum (ESI): 411 (M+H)

Example 31

4-[(5-Chloropyridin-2-yl)methoxy]-1-[4-(2-pyrrolidin-1-ylethyl)phenyl]pyridin-2(1H)-one

(1) Production of 4-hydroxy-1-[4-(2-pyrrolidin-1-ylethyl)phenyl]pyridin-2(1H)-one In the same manner as in Example 19-(1), but changing, in Example 19-(1), the compound obtained in Example 17-(1) to the compound obtained in Example 21-(5), the entitled compound was obtained.

(2) Production of 4-[(5-Chloropyridin-2-yl)methoxy]-1-[4-(2-pyrrolidin-1-ylethyl)phenyl]pyridin-2(1H)-one In the same manner as in Example 19-(2) but changing, in Example 19-(2), the compound obtained in Example 19-(1) to the compound obtained in Example 31-(1), the entitled compound was obtained.
$^1$HNMR (400 MHz, CDCl$_3$, δ ppm): 1.85-2.05 (4H, m), 2.64-3.10 (8H, m), 5.15 (2H, s), 6.02 (1H, d, J=2.7 Hz), 6.09 (1H, dd, J=2.7, 7.7 Hz), 7.24 (1H, d, J=7.7 Hz), 7.28 (2H, d, J=8.5 Hz), 7.33 (2H, d, J=8.5 Hz), 7.43 (1H, d, J=8.4 Hz), 7.73 (1H, dd, J=2.4, 8.4 Hz), 8.58 (1H, d, J=2.4 Hz);
Mass Spectrum (ESI): 410 (M+H)

Example 32

4-[(5-Chloropyridin-2-yl)methoxy]-1-{4-[2-(diethylamino)ethyl]phenyl}pyridin-2(1H)-one

(1) Production of 4-hydroxy-1-{4-[2-(tetrahydro-2H-pyran-2-yloxy)ethyl]phenyl}pyridin-2(1H)-one In the same manner as in Example 19-(1) but changing, in Example 19-(1), the compound obtained in Example 17-(1) to the compound obtained in Example 21-(1), the entitled compound was obtained.

(2) Production of 4-[(5-chloropyridin-2-yl)methoxy]-1-{4-[2-(tetrahydro-2H-pyran-2-yloxy)ethyl]phenyl}pyridin-2(1H)-one A mixture of the compound obtained in (1) (0.99 g, 3.14 mmol), potassium carbonate (0.87 g, 6.29 mmol), 5-chloro-2-methanesulfonyloxymethylpyridine (0.83 g, 3.75 mmol) and DMF (20 mL) was stirred at 80° C. for 6 hours. Water was added to the reaction liquid, the precipitated solid was collected by filtration, dissolved in chloroform, washed with saturated saline, and dried with anhydrous sodium sulfate. The solvent was concentrated under reduced pressure to obtain the entitled compound (1.09 g, 79%).

(3) Production of 1-[4-(2-bromoethyl)phenyl]-4-[(5-chloropyridin-2-yl)methoxy]pyridin-2(1H)-one In the same manner as in Example 21-(3) and (4) but changing, in Examples 21-(3) and (4), the compound obtained in Example 21-(2) to the compound obtained in Example 32-(2), the entitled compound was obtained.

(4) Production of 4-[(5-chloropyridin-2-yl)methoxy]-1-{4-[2-(diethylamino)ethyl]phenyl}pyridin-2(1H)-one In the same manner as in Example 21-(5) but changing, in Example 21-(5), the compound obtained in Example 21-(4) to the compound obtained in Example 32-(3) and changing pyrrolidine to diethylamine, the entitled compound was obtained.
$^1$HNMR (400 MHz, CDCl$_3$, δ ppm): 1.11 (6H, t, J=7.0 Hz), 2.68 (4H, q, J=7.0 Hz), 2.71-2.90 (4H, m), 5.15 (2H, s), 6.02 (1H, d, J=2.7 Hz), 6.09 (1H, dd, J=2.7, 7.6 Hz), 7.25 (1H, d, J=7.6 Hz), 7.27 (2H, d, J=8.7 Hz), 7.31 (2H, d, J=8.7 Hz), 7.44 (1H, d, J=8.3 Hz), 7.73 (1H, dd, J=2.4, 8.3 Hz), 8.58 (1H, d, J=2.4 Hz);
Mass Spectrum (ESI): 412 (M+H)

Examples 33 to 42

In the same manner as in Example 32-(4) but changing diethylamine in Example 32-(4) to corresponding compounds, the compounds of Examples 33 to 42 were obtained.

Example 33

4-[(5-Chloropyridin-2-yl)methoxy]-1-(4-{2-[(2-methoxyethyl)(methyl)amino]ethyl}phenyl)pyridin-2(1H)-one

Using (2-methoxyethyl)methylamine, the entitled compound was synthesized.
$^1$HNMR (400 MHz, CDCl$_3$, δ ppm): 2.37 (3H, s), 2.66 (2H, t, J=5.7 Hz), 2.64-2.74 (2H, m), 2.80-2.90 (2H, m), 3.37 (3H, s), 3.51 (2H, t, J=5.7 Hz), 5.15 (2H, s), 6.02 (1H, d, J=2.7 Hz), 6.08 (1H, dd, J=2.7, 7.7 Hz), 7.24 (1H, d, J=7.7 Hz), 7.25 (2H, d, J=8.4 Hz), 7.30 (2H, d, J=8.4 Hz), 7.43 (1H, d, J=8.4 Hz), 7.73 (1H, dd, J=2.4, 8.4 Hz), 8.58 (1H, d, J=2.4 Hz);
Mass Spectrum (ESI): 428 (M+H)

Example 34

4-[(5-Chloropyridin-2-yl)methoxy]-1-[4-(2-morpholin-4-ylethyl)phenyl]pyridin-2(1H)-one Using morpholine, the entitled compound was synthesized.

$^1$HNMR (400 MHz, CDCl$_3$, δ ppm): 2.45-2.68 (6H, m), 2.80-2.90 (2H, m), 3.70-3.82 (4H, m), 5.15 (2H, s), 6.02 (1H, d, J=2.7 Hz), 6.08 (1H, dd, J=2.7, 7.6 Hz), 7.24 (1H, d, J=7.6 Hz), 7.26 (2H, d, J=8.6 Hz), 7.31 (2H, d, J=8.6 Hz), 7.43 (1H, d, J=8.4 Hz), 7.73 (1H, dd, J=2.5, 8.4 Hz), 8.58 (1H, d, J=2.5 Hz);

Mass Spectrum (ESI): 426 (M+H)

Example 35

4-[(5-Chloropyridin-2-yl)methoxy]-1-(4-{2-[(3R)-3-methoxypyrrolidin-1-yl]ethyl}phenyl)pyridin-2(1H)-one Using (3R)-3-methoxypyrrolidine, the entitled compound was synthesized.

$^1$HNMR (400 MHz, CDCl$_3$, δ ppm): 1.88-2.24 (2H, m), 2.72-3.37 (8H, m), 3.32 (3H, s), 3.95-4.07 (1H, m), 5.15 (2H, s), 6.02 (1H, d, J=2.7 Hz), 6.09 (1H, dd, J=2.7, 7.6 Hz), 7.24 (1H, d, J=7.6 Hz), 7.28 (2H, d, J=8.6 Hz), 7.33 (2H, d, J=8.6 Hz), 7.44 (1H, d, J=8.4 Hz), 7.73 (1H, dd, J=2.5, 8.4 Hz), 8.58 (1H, d, J=2.5 Hz);

Mass Spectrum (ESI): 440 (M+H)

Example 36

4-[(5-Chloropyridin-2-yl)methoxy]-1-(4-{2-[(2-methoxyethyl)amino]ethyl}phenyl)pyridin-2(1H)-one Using 2-methoxyethylamine, the entitled compound was synthesized.

$^1$HNMR (400 MHz, CDCl$_3$, δ ppm): 2.87 (2H, t, J=5.4 Hz), 2.86-2.98 (4H, m), 3.35 (3H, s), 3.53 (2H, t, J=5.4 Hz), 5.15 (2H, s), 6.02 (1H, d, J=2.4 Hz), 6.09 (1H, dd, J=2.4, 7.8 Hz), 7.24 (1H, d, J=7.8 Hz), 7.28 (2H, d, J=8.8 Hz), 7.32 (2H, d, J=8.8 Hz), 7.43 (1H, d, J=8.2 Hz), 7.73 (1H, dd, J=2.4, 8.2 Hz), 8.58 (1H, d, J=2.4 Hz);

Mass Spectrum (ESI): 414 (M+H)

Example 37

4-[(5-Chloropyridin-2-yl)methoxy]-1-{4-[(2-cyclopentylamino)ethyl]phenyl}pyridin-2(1H)-one Using cyclopentylamine, the entitled compound was synthesized.

$^1$HNMR (400 MHz, CDCl$_3$, δ ppm): 1.22-2.00 (8H, m), 2.90 (4H, s), 3.12 (1H, quint, J=6.8 Hz), 5.15 (2H, s), 6.02 (1H, d, J=2.7 Hz), 6.09 (1H, dd, J=2.7, 7.6 Hz), 7.25 (1H, d, J=7.6 Hz), 7.26 (2H, d, J=8.5 Hz), 7.33 (2H, d, J=8.5 Hz), 7.43 (1H, d, J=8.3 Hz), 7.73 (1H, dd, J=2.4, 8.3 Hz), 8.58 (1H, d, J=2.4 Hz);

Mass Spectrum (ESI): 424 (M+H)

Example 38

4-[(5-Chloropyridin-2-yl)methoxy]-1-{4-[(2-isopropylamino)ethyl]phenyl}pyridin-2(1H)-one Using isopropylamine, the entitled compound was synthesized.

$^1$HNMR (400 MHz, CDCl$_3$, δ ppm): 1.10 (6H, d, J=6.3 Hz), 2.80-2.95 (5H, m), 5.15 (2H, s), 6.02 (1H, d, J=2.4 Hz), 6.09 (1H, dd, J=2.4, 7.8 Hz), 7.25 (1H, d, J=7.8 Hz), 7.26 (2H, d, J=8.3 Hz), 7.32 (2H, d, J=8.3 Hz), 7.43 (1H, d, J=8.3 Hz), 7.73 (1H, dd, J=2.4, 8.3 Hz), 8.58 (1H, d,=2.4 Hz);

Mass Spectrum (ESI): 398 (M+H)

Example 39

4-[(5-Chloropyridin-2-yl)methoxy]-1-(4-{2-[(2S)-2-(methoxymethyl)pyrrolidin-1-yl]ethyl}phenyl)pyridin-2(1H)-one Using (2S)-2-(methoxymethyl)pyrrolidine, the entitled compound was synthesized.

$^1$HNMR (400 MHz, CDCl$_3$, δ ppm): 1.42-3.58 (13H, m), 3.36 (3H, s), 5.15 (2H, s), 6.02 (1H, d, J=2.4 Hz), 6.08 (1H, dd, J=2.4, 7.3 Hz), 7.25 (1H, d, J=7.3 Hz), 7.25 (2H, d, J=7.8 Hz), 7.33 (2H, d, J=7.8 Hz), 7.43 (1H, d, J=8.3 Hz), 7.73 (1H, dd, J=2.4, 8.3 Hz), 8.58 (1H, d, J=2.4 Hz);

Mass Spectrum (ESI): 454 (M+H)

Example 40

4-[(5-Chloropyridin-2-yl)methoxy]-1-(4-{2-[(3R)-3-fluoropyrrolidin-1-yl]ethyl}phenyl)pyridin-2(1H)-one Using (3R)-3-fluoropyrrolidine, the entitled compound was synthesized.

$^1$HNMR (400 MHz, CDCl$_3$, δ ppm): 1.98-3.09 (10H, m), 5.15 (2H, s), 5.12-5.18 (1H, m), 6.02 (1H, d, J=2.4 Hz), 6.08 (1H, dd, J=2.4, 7.3 Hz), 7.28 (1H, d, J=7.3 Hz), 7.28 (2H, d, J=8.8 Hz), 7.32 (2H, d, J=8.8 Hz), 7.43 (1H, d, J=8.3 Hz), 7.73 (1H, dd, J=2.4, 8.3 Hz), 8.58 (1H, d, J=2.4 Hz);

Mass Spectrum (ESI): 428 (M+H)

Example 41

4-[(5-Chloropyridin-2-yl)methoxy]-1-(4-{2-[(3S)-3-fluoropyrrolidin-1-yl]ethyl}phenyl)pyridin-2(1H)-one Using (3S)-3-fluoropyrrolidine, the entitled compound was synthesized.

$^1$HNMR (400 MHz, CDCl$_3$, δ ppm): 1.97-3.07 (10H, m), 5.21 (2H, s), 5.15-5.27 (1H, m), 6.02 (1H, d, J=2.9 Hz), 6.08 (1H, dd, J=2.9, 7.3 Hz), 7.26 (1H, d, J=7.3 Hz), 7.27 (2H, d, J=8.3 Hz), 7.32 (2H, d, J=8.3 Hz), 7.43 (1H, d, J=8.3 Hz), 7.73 (1H, dd, J=2.4, 8.3 Hz), 8.58 (1H, d, J=2.4 Hz);

Mass Spectrum (ESI): 428 (M+H)

Example 42

4-[(5-Chloropyridin-2-yl)methoxy]-1-(4-{2-[(3S)-3-methoxypyrrolidin-1-yl]ethyl}phenyl)pyridin-2(1H)-one Using (3S)-3-methoxypyrrolidine, the entitled compound was synthesized.

$^1$HNMR (400 MHz, CDCl$_3$, δ ppm): 1.75-3.08 (10H, m), 3.31 (3H, s), 3.88-4.02 (1H, m), 5.15 (2H, s), 6.02 (1H, d, J=2.9 Hz), 6.08 (1H, dd, J=2.9, 7.6 Hz), 7.24 (1H, d, J=7.6 Hz), 7.25 (2H, d, J=8.3 Hz), 7.31 (2H, d, J=8.3 Hz), 7.43 (1H, d, J=8.3 Hz), 7.73 (1H, dd, J=2.4, 8.3 Hz), 8.58 (1H, d, J=2.4 Hz);

Mass Spectrum (ESI): 440 (M+H)

Example 43

4-[(4-Fluorobenzyl)oxy]-1-(4-{[(3R)-pyrrolidin-3-yloxy]methyl}phenyl)pyridin-2(1H)-one (1) Production of 4-[(4-fluorobenzyl)oxy]-1-[4-(hydroxymethyl)phenyl]pyridin-2(1H)-one Lithiumaluminium hydride (200 mg, 5.27 mmol) was added to a THF (150 mL) suspension of the compound obtained in Example 14-(1) (1.21 g, 3.42 mmol), and stirred at room temperature for 1.5 hours. Water was added to the reaction liquid, then this was made acidic with 1 N hydrochloric acid, extracted with chloroform, and dried with anhydrous magnesium sulfate. The solvent was concentrated under reduced pressure, and the obtained residue was purified by silica gel column chromatography (C-200, methanol:chloroform=3:97 to 1:19) to obtain the entitled compound (0.74 g, 66%).

(2) Production of 4-[(4-fluorobenzyl)oxy]-1-[4-(methanesulfonyloxymethyl)phenyl]pyridin-2(1H)-one In the same manner as in Example 21-(3) but changing in Example 21-(3), the compound obtained in Example 21-(2) to the compound obtained in Example 42-(1), the entitled compound was obtained.

(3) Production of Tert-Butyl 3-({4-{4-[(4-fluorobenzyl)oxy]-2-oxopyridin-1(2H)-yl]benzyl}oxy)pyrrolidine-1-carboxylate Sodium hydride (60% oily, 40 mg, 0.833 mmol) was added to a DMF (2 mL) solution of the compound obtained in Example 42-(2) (110 mg, 0.587 mmol), and stirred at room temperature for 30 minutes. Tert-butyl (3R)-3-hydroxypyrrolidine-1-carboxylate (79 mg, 0.196 mmol) was added, and stirred at room temperature for 1 hour. Water was added to the reaction liquid, and extracted with chloroform. The organic layer was washed with saturated saline, dried with anhydrous magnesium sulfate. The solvent was concentrated under reduced pressure, and the obtained residue was purified by silica gel column chromatography (C-200, methanol:chloroform=1:99 to 3:97) to obtain the entitled compound (42 mg, 43%).

(4) Production of 4-[(4-fluorobenzyl)oxy]-1-(4-{[(3R)-pyrrolidin-3-yloxy]methyl}phenyl)pyridin-2(1H)-one In the same manner as in Example 14-(5) but changing in Example 14-(5), the compound obtained in Example 14-(4) to the compound obtained in Example 43-(3), the entitled compound was obtained.

$^1$HNMR (400 MHz, CDCl$_3$, δ ppm): 1.85-1.99 (2H, m), 2.82-2.93 (2H, m), 3.08-3.19 (2H, m), 4.11-4.18 (1H, m), 4.52 (2H, s), 5.00 (2H, s), 6.03 (1H, d, J=7.8 Hz), 6.04 (1H, s), 7.10 (2H, t, J=8.8 Hz), 7.21 (1H, d, J=7.8 Hz), 7.33 (2H, d, J=8.3 Hz), 7.40 (2H, dd, J=5.4, 8.8 Hz), 7.44 (2H, d, J=8.8 Hz);

Mass Spectrum (ESI): 395 (M+H)

Example 44

4-[(4-Fluorobenzyl)oxy]-1-(4-{[(2S)-pyrrolidin-2-ylmethoxy]methyl}phenyl)pyridin-2(1H)-one (1) Production of Tert-Butyl (2S)-2-[({4-{4-[(4-fluorobenzyl)oxy]-2-oxopyridin-1(2H)-yl]benzyl}oxy)methyl]pyrrolidine-1-carboxylate Sodium hydride (60% oily, 60 mg, 1.25 mmol) was added at a time to a DMF (5 mL) solution of the compound obtained in Example 42-(2) (100 mg, 0.248 mmol) and tert-butyl (2S)-2-(hydroxymethyl)pyrrolidine-1-carboxylate (250 mg, 1.24 mmol), and stirred at room temperature for 3 hours. Saturated saline was added to the reaction liquid, extracted with chloroform, dried with anhydrous magnesium sulfate. The solvent was concentrated under reduced pressure, and the obtained residue was purified by silica gel column chromatography (C-200, methanol:chloroform=1:99 to 3:97) to obtain the entitled compound (126 mg, 100%).

(2) Production of 4-[(4-fluorobenzyl)oxy]-1-(4-{[(3R)-pyrrolidin-3-yloxy]methyl}phenyl)pyridin-2(1H)-one In the same manner as in Example 43-(4) but changing, in Example 43-(4), the compound obtained in Example 43-(3) to the compound obtained in Example 44-(1), the entitled compound was obtained.

$^1$HNMR (400 MHz, CDCl$_3$, δ ppm): 1.36-2.13 (4H, m), 2.86-3.04 (2H, m), 3.31-3.39 (1H, m), 3.42 (1H, t, J=7.8 Hz), 3.49-3.55 (1H, m), 4.58 (1H, d, J=12.2 Hz), 4.59 (1H, d, J=12.2 Hz), 5.00 (2H, s), 6.03 (1H, d, J=7.8 Hz), 6.04 (1H, s), 7.10 (2H, t, J=8.8 Hz), 7.22 (1H, d, J=7.8 Hz), 7.33 (2H, d, J=8.3 Hz), 7.40 (2H, dd, J=5.4, 8.8 Hz), 7.45 (2H, d, J=8.3 Hz);

Mass Spectrum (ESI): 409 (M+H)

Examples 45 to 49

In the same manner as in Example 44 but changing the (2S)-2-(hydroxymethyl)pyrrolidine-1-carboxylate in Example 44-(1) to corresponding compounds, obtained were the compounds of Examples 45 to 49.

Example 45

4-[(4-Fluorobenzyl)oxy]-1-(4-{[(2R)-pyrrolidin-2-ylmethoxy]methyl}phenyl)pyridin-2(1H)-one Using tert-butyl (2R)-2-(hydroxymethyl)pyrrolidine-1-carboxylate, the entitled compound was synthesized.

$^1$HNMR (400 MHz, CDCl$_3$, δ ppm): 1.39-1.49 (1H, m), 1.69-1.94 (3H, m), 2.86-2.94 (1H, m), 2.96-3.04 (1H, m), 3.29-3.38 (1H, m), 3.39-3.44 (1H, m), 3.49-3.55 (1H, m), 4.57 (1H, d, J=12.7 Hz), 4.59 (1H, d, J=12.7 Hz), 5.00 (2H, s), 6.03 (1H, d, J=7.8 Hz), 6.04 (1H, s), 7.10 (2H, t, J=8.8 Hz), 7.22 (1H, d, J=7.8 Hz), 7.33 (2H, d, J=8.3 Hz), 7.40 (2H, dd, J=5.4, 8.8 Hz), 7.44 (2H, d, J=8.3 Hz);

Mass Spectrum (ESI): 409 (M+H)

Example 46

4-[(4-Fluorobenzyl)oxy]-1-[4-({[(3S)-5-isopropylpyrrolidin-3-yl]oxy}methyl)phenyl]pyridin-2(1H)-one Using tert-butyl (2S,4S)-4-hydroxy-2-isopropylpyrrolidine-1-carboxylate, the entitled compound was synthesized.

$^1$HNMR (400 MHz, CDCl$_3$, δ ppm): 0.94 (3H, d, J=6.8 Hz), 1.01 (3H, d, J=6.8 Hz), 1.44-1.54 (1H, m), 1.60-1.72 (1H, m), 2.16-2.22 (1H, m), 2.69 (1H, q, J=8.1 Hz), 2.83 (1H, dd, J=5.4, 12.2 Hz), 3.18 (1H, d, J=12.2 Hz), 4.08-4.15 (1H, m), 4.50 (2H, s), 5.00 (2H, s), 6.02 (1H, d, J=7.8 Hz), 6.04 (1H, s), 7.10 (2H, t, J=8.8 Hz), 7.21 (1H, d, J=7.8 Hz), 7.33 (2H, d, J=8.3 Hz), 7.40 (2H, dd, J=5.4, 8.8 Hz), 7.44 (2H, d, J=8.3 Hz);

Mass Spectrum (ESI): 437 (M+H)

Example 47

4-[(4-Fluorobenzyl)oxy]-1-(4-{[(3S)-pyrrolidin-3-yloxy]methyl}phenyl)pyridin-2(1H)-one Using tert-butyl (3S)-3-hydroxypyrrolidine-1-carboxylate, the entitled compound was synthesized.

$^1$HNMR (400 MHz, CDCl$_3$, δ ppm): 1.88-1.96 (2H, m), 2.84-2.93 (2H, m), 3.08-3.18 (2H, m), 4.12-4.17 (1H, m), 4.52 (2H, s), 5.00 (2H, s), 6.03 (1H, d, J=7.8 Hz), 6.04 (1H, s), 7.10 (2H, t, J=8.8 Hz), 7.21 (1H, d, J=7.8 Hz), 7.33 (2H, d, J=8.3 Hz), 7.40 (2H, dd, J=5.4, 8.8 Hz), 7.44 (2H, d, J=8.3 Hz);

Mass Spectrum (ESI): 395 (M+H)

Example 48

4-[(4-Fluorobenzyl)oxy]-1-[4-({[(3R,5S)-5-isopropylpyrrolidin-3-yl]oxy}methyl)phenyl]pyridin-2(1H)-one Using tert-butyl (2S,4R)-4-hydroxy-2-isopropylpyrrolidine-1-carboxylate, the entitled compound was synthesized.

$^1$HNMR (400 MHz, CDCl$_3$, δ ppm): 0.90 (3H, d, J=6.3 Hz), 0.98 (3H, d, J=6.3 Hz), 1.44-1.56 (2H, m), 2.00-2.08 (1H, m), 2.93-3.00 (1H, m), 2.98-3.04 (1H, m), 3.17-3.24 (1H, m), 4.09-4.17 (1H, m), 4.51 (1H, d, J=12.2 Hz), 4.53 (1H, d, J=12.2 Hz), 5.00 (2H, s), 6.03 (1H, d, J=7.8 Hz), 6.04 (1H, s), 7.10 (2H, t, J=8.8 Hz), 7.21 (1H, d, J=7.8 Hz), 7.33 (2H, d, J=8.3 Hz), 7.40 (2H, dd, J=5.4, 8.8 Hz), 7.44 (2H, d, J=8.3 Hz);

Mass Spectrum (ESI): 437 (M+H)

Example 49

4-[(4-Fluorobenzyl)oxy]-1-{4-[(2-pyrrolidin-1-ylethoxy)methyl]phenyl}pyridin-2(1H)-one Using 2-pyrrolidin-1-ylethanol, the entitled compound was synthesized.

$^1$HNMR (400 MHz, CDCl$_3$, δ ppm): 1.78-2.06 (4H, m), 2.54-2.95 (6H, m), 3.63-3.79 (2H, m), 4.59 (2H, s), 5.00 (2H, s), 6.03 (1H, d, J=7.3 Hz), 6.04 (1H, s), 7.10 (2H, t, J=8.3 Hz), 7.22 (1H, d, J=7.3 Hz), 7.33 (2H, d, J=8.3 Hz), 7.40 (2H, dd, J=5.4, 8.3 Hz), 7.45 (2H, d, J=8.3 Hz);

Mass Spectrum (ESI): 423 (M+H)

Example 50

4-[(4-Fluorobenzyl)oxy]-1-[4-(2-pyrrolidin-1-ylpropyl)phenyl]pyridin-2(1H)-one (1) Production of 4-[(4-fluorobenzyl)oxy]-1-[4-(2-oxopropyl)phenyl]pyridin-2(1H)-one In the same manner as in Example 1-(1) but changing (2E)-3-(4-bromophenyl)-2-propen-1-ol in Example 1-(1) to 1-(4-bromophenyl)acetone, the entitled compound was obtained.

(2) Production of 4-[(4-fluorobenzyl)oxy]-1-[4-(2-pyrrolidin-1-ylpropyl)phenyl]pyridin-2(1H)-one In the same manner as in Example 16 but changing, in Example 16, the compound obtained in Example 15 to the compound obtained in Example 50-(1) and changing aqueous 37% formalin solution to pyrrolidine, the entitled compound was obtained.

$^1$HNMR (400 MHz, CDCl$_3$, δ ppm): 1.37 (3H, d, J=6.3 Hz), 1.98-2.17 (2H, m), 2.17-2.35 (2H, m), 2.83-3.04 (3H, m), 3.32-3.54 (2H, m), 3.64-3.90 (2H, m), 5.01 (2H, s), 6.04 (1H, s), 6.05 (1H, d, J=7.2 Hz), 7.10 (2H, t, J=8.7 Hz), 7.23 (1H, d, J=7.2 Hz), 7.34 (4H, s), 7.40 (2H, dd, J=5.1, 8.7 Hz);

Mass Spectrum (ESI): 407 (M+H)

Example 51

4-[(4-Fluorobenzyl)oxy]-1-[4-(1-methoxy-2-pyrrolidin-1-ylethyl)phenyl]pyridin-2(1H)-one (1) Production of 1-(4-bromophenyl)-2-pyrrolidin-1-ylethanone Diisopropylethylamine (6.2 mL, 36.0 mmol) and pyrrolidine (2.3 mL, 27.6 mmol) were added to a THF (90 mL) solution of 2-bromo-1-(4-bromophenyl)ethanone (5.0 g, 18.0 mmol), and stirred at room temperature for 2 hours. Saturated sodium bicarbonate water was added to the reaction liquid, extracted with chloroform, and dried with anhydrous magnesium sulfate. The solvent was concentrated under reduced pressure and the obtained residue was purified by silica gel column chromatography (C-200, methanol:chloroform=1:99 to 3:97) to obtain the entitled compound (2.35 g, 49%).

(2) Production of 1-(4-bromophenyl)-2-pyrrolidin-1-ylethanol

Sodium borohydride (500 mg, 13.2 mmol) was added to an ethanol (100 mL) solution of the compound obtained in Example 51-(1) (2.35 g, 18.0 mmol), and stirred at room temperature for 1.5 hours. Acetone was added to the reaction liquid, the solvent was concentrated under reduced pressure, then saturated saline was added to the obtained residue, extracted with chloroform and dried with anhydrous magnesium sulfate. The solvent was concentrated under reduced pressure, and the obtained residue was purified by silica gel column chromatography (C-200, methanol:chloroform=3:97 to 1:19 to 1:10) to obtain the entitled compound (1.17 g, 49%).

(3) Production of 1-[2-(4-bromophenyl)-2-methoxyethyl]pyrrolidine

In the same manner as in Example 43-(3) but changing in Example 43-(3), the compound obtained in Example 43-(2) to the compound obtained in Example 51-(2) and changing tert-butyl (2S)-2-(hydroxymethyl)pyrrolidine-1-carboxylate to iodomethane, the entitled compound was obtained.

(4) Production of 4-[(4-fluorobenzyl)oxy]-1-[4-(1-methoxy-2-pyrrolidin-1-ylethyl)phenyl]pyridin-2(1H)-one In the same manner as in Example 1-(1) but changing in Example 1-(1), (2E)-3-(4-bromophenyl)-2-propen-1-ol to the compound obtained in Example 51-(3), the entitled compound was obtained.
$^1$HNMR (400 MHz, CDCl$_3$, δ ppm): 1.74-1.90 (4H, m), 2.44-2.93 (6H, m), 3.29 (3H, s), 4.30-4.50 (1H, m), 5.00 (2H, s), 6.04 (1H, d, J=7.8 Hz), 6.05 (1H, s), 7.10 (2H, t, J=8.8 Hz), 7.24 (1H, d, J=7.8 Hz), 7.35 (2H, d, J=8.3 Hz), 7.40 (2H, dd, J=5.4, 8.8 Hz), 7.43 (2H, d, J=8.3 Hz);
Mass Spectrum (ESI): 423 (M+H)

Example 52

4-[(4-Fluorobenzyl)oxy]-1-[4-(3-pyrrolidin-1-ylcyclobutyl)phenyl]pyridin-2(1H)-one (1) Production of 1-[3-(4-bromophenyl)cyclobutyl]pyrrolidine In the same manner as in Example 50-(2) but changing in Example 50-(2), the compound obtained in Example 50-(1) to 3-(4-bromophenyl)cyclobutanone, the entitled compound was obtained.

(2) Production of 4-[(4-fluorobenzyl)oxy]-1-[4-(3-pyrrolidin-1-ylcyclobutyl)phenyl]pyridin-2(1H)-one In the same manner as in Example 1-(1) but changing (2E)-3-(4-bromophenyl)-2-propen-1-ol in Example 1-(1) to the compound obtained in Example 52-(1), the entitled compound was obtained.
$^1$HNMR (400 MHz, CDCl$_3$, δ ppm): 1.75-1.92 (4H, m), 2.04-2.66 (8H, m), 2.83-3.00 (1H, m), 3.13-3.27 (1H, m), 4.99 (2H, s), 6.02 (1H, dd, J=2.9, 7.3 Hz), 6.04 (1H, d, J=2.9 Hz), 7.10 (2H, t, J=8.8 Hz), 7.21 (1H, d, J=7.3 Hz), 7.26 (2H, d, J=8.3 Hz), 7.36 (2H, d, J=8.8 Hz), 7.40 (2H, dd, J=5.4, 8.8 Hz);
Mass Spectrum (ESI): 419 (M+H)

Example 53

4-[(4-Fluorobenzyl)oxy]-1-[4-(trans-3-pyrrolidin-1-ylcyclobutyl)phenyl]pyridin-2(1H)-one (1) Production of cis-3-(4-bromophenyl)cyclobutanol At −78° C., 1.0 M tri(tert-butoxy)lithiumaluminium hydride (24 mL, 24 mmol) was added to a THF (20 mL) solution of 3-(4-bromophenyl)cyclobutanone (4.53 g, 20.1 mmol), and stirred at the same temperature for 1.5 hours. Saturated ammonium chloride water and 1 N hydrochloric acid were added to the reaction liquid, extracted with ethyl acetate, dried with anhydrous magnesium sulfate. The solvent was concentrated under reduced pressure, the obtained residue was purified by silica gel column chromatography (C-200, ethyl acetate:hexane=1:4 to 3:7) to obtain the entitled compound (3.04 g, 66%).

(2) Production of 2-{[cis-3-(4-bromophenyl)cyclobutyl]oxy}tetrahydro-2H-pyran

In the same manner as in Example 17-(1) but changing 3-(4-iodophenyl)propan-1-ol in Example 17-(1) to the compound obtained in Example 53-(1), the entitled compound was obtained.

(3) Production of 4-[(4-fluorobenzyl)oxy]-1-{4-[cis-3-(tetrahydro-2H-pyran-2-yloxy)cyclobutyl]phenyl}pyridin-2(1H)-one In the same manner as in Example 1-(1) but changing (2E)-3-(4-bromophenyl)-2-propen-1-ol in Example 1-(1) to the compound obtained in Example 53-(2), the entitled compound was obtained.

(4) Production of 4-[(4-fluorobenzyl)oxy]-1-[4-(cis-3-(hydroxycyclobutyl)phenyl)pyridin-2(1H)-one In the same manner as in Example 17-(4) but changing, in Example 17-(4), the compound obtained in Example 17-(3) to the compound obtained in Example 53-(3), the entitled compound was obtained.

(5) Production of 4-[(4-fluorobenzyl)oxy]-1-[4-(trans-3-pyrrolidin-1-ylcyclobutyl)phenyl]pyridin-2(1H)-one In the same manner as in Example 21-(3) and (5) but changing, in Example 21-(3) and (5), the compound obtained in Example 21-(2) to the compound obtained in Example 53-(4), the entitled compound was obtained.
$^1$HNMR (400 MHz, CDCl$_3$, δ ppm): 1.78-1.96 (4H, m), 2.26-2.36 (2H, m), 2.47-2.68 (6H, m), 3.01-3.15 (1H, m), 3.64-3.76 (1H, m), 5.00 (2H, s), 6.03 (1H, dd, J=2.9, 7.3 Hz), 6.05 (1H, d, J=2.9 Hz), 7.10 (2H, t, J=8.5 Hz), 7.23 (1H, d, J=7.3 Hz), 7.29 (2H, d, J=8.3 Hz), 7.36 (2H, d, J=8.3 Hz), 7.40 (2H, dd, J=5.4, 8.5 Hz);
Mass Spectrum (ESI): 419 (M+H)

Example 54

4-[(4-Fluorobenzyl)oxy]-1-[4-(cis-3-pyrrolidin-1-ylcyclobutyl)phenyl]pyridin-2(1H)-one (1) Production of 4-[(4-fluorobenzyl)oxy]-1-[4-(trans-3-(hydroxycyclobutyl)phenyl)pyridin-2(1H)-one Diisopropyl azodicarboxylate (0.32 mL, 1.63 mmol) was added to a THF (20 mL) solution of the compound obtained in Example 53-(4) (195 mg, 0.534 mmol), triphenyl phosphine (420 mg, 1.60 mmol) and acetic acid (90 µL, 1.57 mmol), and stirred overnight at room temperature. The reaction liquid was concentrated under reduced pressure, and the obtained residue was purified by silica gel column chromatography (C-200, methanol:chloroform=1:99 to 3:97) to obtain a crude acetate (1.01 g). Aqueous 4 N sodium hydroxide solution (5 mL) was added to a methanol (20 mL) solution of the crude acetate (1.01 g), and stirred at 90° C. for 2 hours. The reaction liquid was diluted with water, extracted with chloroform and dried with anhydrous magnesium sulfate. The solvent was concentrated under reduced pressure, and the obtained residue was purified by silica gel column chromatography (C-200, methanol:chloroform=3:97 to 1:19) to obtain the entitled compound (122 mg, 63%).

(2) Production of 4-[(4-fluorobenzyl)oxy]-1-[4-(cis-3-pyrrolidin-1-ylcyclobutyl)phenyl]pyridin-2(1H)-one In the same manner as in Example 53-(5) but changing in Example 53-(5), the compound obtained in Example 53-(4) to the compound obtained in Example 54-(1), the entitled compound was obtained.

$^1$HNMR (400 MHz, CDCl$_3$, δ ppm): 1.80-1.95 (4H, m), 2.05-2.80 (8H, m), 2.87-3.09 (1H, m), 3.21 (1H, tt, J=4.3, 10.0 Hz), 4.99 (2H, s), 6.02 (1H, dd, J=2.9, 7.3 Hz), 6.04 (1H, d, J=2.9 Hz), 7.10 (2H, t, J=8.3 Hz), 7.21 (1H, d, J=7.3 Hz), 7.27 (2H, d, J=8.8 Hz), 7.39 (2H, d, J=8.8 Hz), 7.39 (2H, dd, J=5.4, 8.3 Hz);

Mass Spectrum (ESI): 419 (M+H)

Reference Example 1

Tert-Butyl (2S,4R)-4-hydroxy-2-isopropylpyrrolidine-1-carboxylate (1) Production of Tert-Butyl (2S,4R)-4-{[tert-butyl(dimethyl)silyl]oxy}-2-(1-hydroxy-1-methylethyl)pyrrolidine-1-carboxylate 3.0 M methylmagnesium bromide (2.0 mL, 6.0 mmol) was added to an ether (15 mL) solution of 1-tert-butyl 2-methyl (2S,4R)-4-{[tert-butyl(dimethyl)silyl]oxy}pyrrolidine-1-carboxylate (1.0 g, 2.79 mmol), and stirred at room temperature for 45 minutes. Saturated ammonium chloride water was added to the reaction liquid, extracted with ethyl acetate, and dried with anhydrous magnesium sulfate. The solvent was concentrated under reduced pressure to obtain the entitled compound (0.97 g, 97%).

(2) Production of Tert-Butyl (2S,4R)-4-{[tert-butyl(dimethyl)silyl]oxy}-2-isopropenylpyrrolidine-1-carboxylate Pyridine (0.44 mL, 5.44 mmol) and thionyl chloride (0.30 mL, 4.11 mmol) were added to a chloroform (30 mL) solution of the compound obtained in Reference Example 1-(1) (0.97 g, 2.70 mmol), and stirred overnight at room temperature. Saturated sodium bicarbonate water was added to the reaction liquid, extracted with chloroform, and dried with anhydrous magnesium sulfate. The solvent was concentrated under reduced pressure, and the obtained residue was purified by silica gel column chromatography (C-200, ethyl acetate:hexane=1:9 to 1:4) to obtain the entitled compound (258 mg, 28%).

(3) Production of Tert-Butyl (2S,4R)-4-{[tert-butyl(dimethyl)silyl]oxy}-2-isopropylpyrrolidine-1-carboxylate In the same manner as in Example 19-(1) but changing, in Example 19-(1), the compound obtained in Example 17-(1) to the compound obtained in Reference Example 1-(2), the entitled compound was obtained.

(4) Production of Tert-Butyl (2S,4R)-4-hydroxy-2-isopropylpyrrolidine-1-carboxylate 1.0 M tetrabutylammonium fluoride (1.5 mL, 1.5 mmol) was added to a THF (5 mL) solution of the compound obtained in Reference Example 1-(3) (237 mg, 0.69 mmol), and stirred at room temperature for 1 hour. Saturated saline was added to the reaction liquid, extracted with ethyl acetate and dried with anhydrous magnesium sulfate. The solvent was concentrated under reduced pressure, and the obtained residue was purified by silica gel column chromatography (C-200, ethyl acetate:hexane=3:7 to 1:1) to obtain the entitled compound (162 mg, 100%).

Reference Example 2

Tert-Butyl (2S,4S)-4-hydroxy-2-isopropylpyrrolidine-1-carboxylate

In the same manner as in Reference Example 1 but changing 1-tert-butyl 2-methyl (2S,4R)-4-{[tert-butyl(dimethyl)silyl]oxy}pyrrolidine-1-carboxylate in Reference Example 1-(1) to 1-tert-butyl 2-methyl (2S,4S)-4-{[tert-butyl(dimethyl)silyl]oxy}pyrrolidine-1-carboxylate, the entitled compound was obtained.

INDUSTRIAL APPLICABILITY

The compounds of the invention have an MCH-1R antagonistic effect and are useful, for example, as a preventive or a remedy for metabolic disorders such as obesity, diabetes, hormone disorder, hyperlipidemia, gout, fatty liver, hepatitis, cirrhosis; cardiovascular disorders such as stenocardia, acute or congestive heart failure, myocardial infarction, coronary atherosclerosis, hypertension, renal diseases, electrolyte abnormality; central and peripheral nervous system disorders such as bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence, alcoholism; reproductive disorders such as infertility, preterm labor and sexual dysfunction; and digestive disorders, respiratory disorders, cancer or pigmentation et al.

The invention claimed is:
1. A compound of formula I, or a pharmaceutically-acceptable salt thereof; wherein:

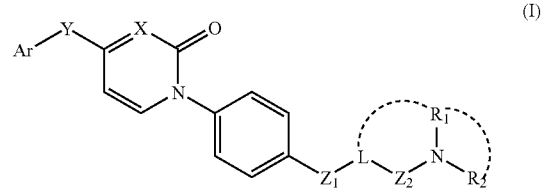

$R_1$ and $R_2$ are each independently selected from: a hydrogen atom, or a lower alkyl group optionally substituted with one or more substituents, and $R_1$, taken together with L, $Z_2$ and the nitrogen atom adjacent to $R_1$, may form an aliphatic nitrogen-containing hetero ring optionally substituted with one or more substituents, and $R_1$ and $R_2$, taken together with the nitrogen atom to which they bond, may form an aliphatic nitrogen-containing hetero ring optionally substituted with one or more substituents;

X represents a methine group optionally substituted with a halogen;

Y represents —CH$_2$—O—, —CH=CH— or —CH$_2$—CH$_2$—;

Z$_1$ represents a single bond, a C$_{1-4}$ alkylene group optionally substituted with one or more substituents, a C$_{1-4}$ alkylene-O— optionally substituted with one or more substituents, a C$_{1-3}$ alkylene-O—C$_{1-3}$ alkylene group optionally substituted with one or more substituents, a C$_{2-4}$ alkenylene group optionally substituted with one or more substituents, or —NR—, R represents a hydrogen atom, or a lower alkyl group optionally substituted with one or more substituents;

Z$_2$ represents a single bond or a C$_{1-4}$ alkylene group optionally substituted with one or more substituents;

L represents a methylene group optionally substituted with one or more substituents, or a C$_{3-8}$ cycloalkylene group optionally substituted with one or more substituents, or L, taken together with Z$_2$, R$_1$ and the nitrogen atom adjacent to R$_1$, may form an aliphatic nitrogen-containing hetero ring optionally substituted with one or more substituents; provided that, when Z$_1$ and Z$_2$ are single bonds at the same time, then L is not a methylene group;

Ar represents an aromatic carbocyclic group optionally substituted with one or more substituents, or an aromatic heterocyclic group optionally substituted with one or more substituents.

2. The compound, or the pharmaceutically-acceptable salt thereof, of claim 1, wherein Y is —CH$_2$—O— or —CH=CH—.

3. The compound, or the pharmaceutically-acceptable salt thereof, of claim 1, wherein Z$_1$ is a single bond, a methylene group optionally substituted with one or more substituents, an ethylene group optionally substituted with one or more substituents, a methylene-O— optionally substituted with one or more substituents, a methylene-O-methylene group optionally substituted with one or more substituents, an ethylene-O— optionally substituted with one or more substituents, or a vinylene group optionally substituted with one or more substituents.

4. The compound, or the pharmaceutically-acceptable salt thereof, of claim 1, wherein Z$_2$ is a single bond, or a methylene group optionally substituted with one or more substituents.

5. The compound, or the pharmaceutically-acceptable salt thereof, of claim 1, wherein L is a methylene group optionally substituted with one or more substituents, or a cyclobutylene group optionally substituted with one or more substituents.

6. The compound, or the pharmaceutically-acceptable salt thereof, of claim 1, wherein R$_1$, taken together with L, Z$_2$ and the nitrogen atom adjacent to R$_1$, forms an azetidinyl optionally substituted with one or more substituents, a pyrrolidinyl optionally substituted with one or more substituents, or a piperidinyl optionally substituted with one or more substituents.

7. The compound, or the pharmaceutically-acceptable salt thereof, of claim 1, wherein R$_1$ and R$_2$ are each independently selected from a hydrogen, a methyl group, an ethyl group, an isopropyl group, an n-propyl group, an n-butyl group and a 2-pyridylmethyl group.

8. The compound, or the pharmaceutically-acceptable salt thereof, of claim 1, wherein R$_1$ and R$_2$, taken together with the nitrogen atom to which they bond, form an azetidinyl optionally substituted with one or more substituents, a pyrrolidinyl substituted with one or more substituents, or a piperidinyl optionally substituted with one or more substituents.

9. The compound, or the pharmaceutically-acceptable salt thereof, of claim 1, wherein Ar is a phenyl optionally substituted with one or more substituents, or a pyridinyl optionally substituted with one or more substituents.

10. The compound, or the pharmaceutically-acceptable salt thereof, of claim 1, wherein the substituent is selected from a group consisting of a fluorine atom, a chlorine atom, a methyl group, an ethyl group, a trifluoromethyl group, a difluoromethoxy group and a trifluoromethoxy group.

11. The compound, or the pharmaceutically-acceptable salt thereof, of claim 1, wherein:

R$_1$ and R$_2$ are each independently selected from a hydrogen, a methyl group, an ethyl group, an isopropyl group, an n-propyl group, an n-butyl group, a 2-pyridylmethyl group and R$_1$, taken together with L, Z$_2$ and the nitrogen atom adjacent to R$_1$, forms an azetidinyl optionally substituted with one or more substituents, a pyrrolidinyl optionally substituted with one or more substituents, or a piperidinyl optionally substituted with one or more substituents, and R$_1$ and R$_2$, taken together with the nitrogen atom to which they bond, form an azetidinyl optionally substituted with one or more substituents, a pyrrolidinyl substituted with one or more substituents, or a piperidinyl optionally substituted with one or more substituents;

X is a methine group optionally substituted with a halogen;

Y is —CH$_2$—O— or —CH=CH—;

Z$_1$ is a single bond, a methylene group optionally substituted with one or more substituents, an ethylene group optionally substituted with one or more substituents, a methylene-O— optionally substituted with one or more substituents, a methylene-O-methylene group optionally substituted with one or more substituents, an ethylene-O— optionally substituted with one or more substituents, or a vinylene group optionally substituted with one or more substituents;

Z$_2$ is a single bond, or a methylene group optionally substituted with one or more substituents;

L is a methylene group optionally substituted with one or more substituents, or a cyclobutylene group optionally substituted with one or more substituents; and Ar is a phenyl optionally substituted a fluorine atom, a chlorine atom, a methyl group, an ethyl group, a trifluoromethyl group, a difluoromethoxy group and a trifluoromethoxy group, or a pyridinyl optionally substituted with a fluorine atom, a chlorine atom, a methyl group, an ethyl group, a trifluoromethyl group, a difluoromethoxy group and a trifluoromethoxy group.

12. The compound, or the pharmaceutically-acceptable salt thereof, of claim 1, wherein the compound of formula I is selected from a group consisting of:

4-[(4-chlorobenzyl)oxy]-1-(4-{(1E)-3-[ethyl(methyl)amino]-1-propen-1-yl}phenyl)pyridin-2(1H)-one, 4-[(4-chlorobenzyl)oxy]-1-(4-{(1E)-3-[propyl(methyl)amino]-1-propen-1-yl}phenyl)pyridin-2(1H)-one, 4-[(4-chlorobenzyl)oxy]-1-(4-{(1E)-3-[isopropyl(methyl)amino]-1-propen-1-yl}phenyl)pyridin-2(1H)-one, 4-[(4-chlorobenzyl)oxy]-1-(4-{(1E)-3-[butyl(methyl)amino]-1-propen-1-yl}phenyl)pyridin-2(1H)-one, 4-[(4-chlorobenzyl)oxy]-1-(4-[(1E)-3-(dimethylamino)-1-propen-1-yl]phenyl)pyridin-2(1H)-one, 4-[(4-fluorobenzyl)oxy]-1-{4-[(2-pyrrolidin-1-ylethyl)amino]phenyl}pyridin-2(1H)-one, 4-[(4-fluorobenzyl)oxy]-1-(4-{2-[(3S)-3-methoxypyrrolidin-1-yl]ethyl}phenyl)pyridin-2(1H)-one, 4-[(5-chloropyridin-2-yl)methoxy]-1-{4-[2-(diethylamino)ethyl]phenyl}pyridin-2(1H)-one, 4-[(5-chloropyridin-2-yl)methoxy]-1-{4-[(2-cyclopentylamino)ethyl]phenyl}pyridin-2(1H)-one, and 4-[(4-fluorobenzyl)oxy]-1-[4-(trans-3-pyrrolidin-1-ylcyclobutyl)phenyl]pyridin-2(1H)-one.

13. The compound, or the pharmaceutically-acceptable salt thereof, of claim 1, wherein the compound of formula I is selected from a group consisting of:

4-[(4-chlorobenzyl)oxy]-1-(4-{(1E)-3-[propyl(methyl)amino]-1-propen-1-yl}phenyl)pyridin-2(1H)-one, 4-[(4-chlorobenzyl)oxy]-1-(4-{(1E)-3-[butyl(methyl)amino]-1-propen-1-yl}phenyl)pyridin-2(1H)-one, 4-[(4-fluorobenzyl)oxy]-1-{4-[(2-pyrrolidin-1-ylethyl)amino]phenyl}pyridin-2(1H)-one, 4-[(5-chloropyridin-2-yl)methoxy]-1-{4-[(2-cyclopentylamino)ethyl]phenyl}pyridin-2(1H)-one, and 4-[(4-fluorobenzyl)oxy]-1-[4-(trans-3-pyrrolidin-1-ylcyclobutyl)phenyl]pyridin-2(1H)-one.

14. A melanin concentrating hormone receptor antagonist comprising a compound or a pharmaceutically-acceptable salt thereof of claim 1 as the active ingredient.

15. A pharmaceutical composition comprising a pharmaceutically-acceptable carrier and a compound, or a pharmaceutically-acceptable salt thereof, of claim 1.

* * * * *